(12) United States Patent
Lorsch et al.

(10) Patent No.: US 8,828,976 B2
(45) Date of Patent: Sep. 9, 2014

(54) IDENTIFICATION AND USE OF COMPOUNDS THAT AFFECT THE FIDELITY OF EUKARYOTIC TRANSLATION INITIATION CODON SELECTION

(75) Inventors: Jon R. Lorsch, Towson, MD (US); Julie Ellen Takacs, Baltimore, MD (US); Timothy Brian Neary, Baldwin, MD (US)

(73) Assignee: The Johns Hopkins University, Baltimore, MD (US)

( * ) Notice: Subject to any disclaimer, the term of this patent is extended or adjusted under 35 U.S.C. 154(b) by 69 days.

(21) Appl. No.: 13/051,610

(22) Filed: Mar. 18, 2011

(65) Prior Publication Data

US 2011/0230451 A1    Sep. 22, 2011

Related U.S. Application Data

(60) Provisional application No. 61/315,240, filed on Mar. 18, 2010.

(51) Int. Cl.
*A61K 31/655*    (2006.01)

(52) U.S. Cl.
USPC ............ 514/150; 514/307; 514/312; 514/297

(58) Field of Classification Search
USPC .................................. 514/150, 307, 312, 297
See application file for complete search history.

(56) References Cited

U.S. PATENT DOCUMENTS 6,093,725 A * 7/2000 Cook et al. .................... 514/297

OTHER PUBLICATIONS

Amrani et al., *Nat. Rev. Mol. Cell Biol.*, vol. 7, No. 6, pp. 415-425, 2006.
Bastide et al., Nucleic Acids Res., vol. 36, pp. 2434-2445, 2008.
Blackwood et al., Mol. Biol. Cell, vol. 5, pp. 597-609, 1994.
Castilho-Valavicius et al., *Genetics*, vol. 124, No. 3, pp. 483-495, 1988.
Cencig et al., Oncogene, vol. 23, pp. 267-277, 2004.
Chen et al., *J. Biol. Chem.* vol. 283, No. 6, pp. 3173-3180, 2008.
Cheung et al., *Genes Dev.*, vol. 21, No. 10, pp. 1217-1230, 2007.
Cigan et al., *Mol. Cell Biol.*, vol. 8, No. 7, pp. 2964-2975, 1988.
Cigan et al., *Science*, vol. 242, No. 4875, pp. 93-97, 1988.
Clements et al., *Mol. Cell Biol.*, vol. 8, No. 10, pp. 4533-4536, 1988.
Donahue et al., *Cell*, vol. 54, No. 5, pp. 621-632, 1988.
Donahue et al., *Mol. Cell Biol.*, vol. 8, No. 7, pp. 2955-2963, 1988.
Fazzio et al., Mol. Cell Biol., vol. 21, no. 19, pp. 6450-6460, 2001.
Fekete et al., *EMBO J.*, vol. 24, No. 20, pp. 3588-3601, 2005.

Gershon et al., *J. Pharm. Sci.*, vol. 80, No. 6, pp. 542-544, 1991.
Hamilton et al., *Nucleic Acids Res.*, vol. 15, No. 8, pp. 3581-2593, 1987.
He et al., *Mol. Cell. Biol.*, vol. 23, No. 15, pp. 5431- 5445, 2003.
Huang et al., *Genes Dev.*, vol. 11, No. 18, pp. 2396-2413, 1997.
Ingolia et al., Science, vol. 324, No. 5924, pp. 218-223, 2009.
Ivanov. et al., Proc. Natl. Acad. Sci. U.S.A., vol. 105, pp. 10079-10084, 2008.
Jackson et al., Nat. Rev. Mol. Cell. Biol., vol. 11, No. 2, pp. 113-127, 2010.
Kolitz et al., RNA, vol. 15, No. 1, pp. 138-152, 2009.
Kozak M., Cell, vol. 44, No. 2, pp. 283-292, 1986.
Kozak M., Nucleic Acids Res., vol. 15, No. 20, pp. 8125-8148, 1987.
Kung et al., Proc. Natl. Acad. Sci. U. S. A., vol. 102, No. 10, pp. 3587-3592, 2005.
Lorsch et al., J. Biol. Chem., vol. 285, No. 21203-21207, 2010.
Lu et al., Biol. Chem. Hoppe Seyler, vol. 377, No. 6, pp. 373-384, 1996.
McNabb et al., Eukaryot. Cell, vol. 4, No. 9, pp. 1539-1549, 2005.
Meijer et al., Biochem. J., vol. 367(Pt.1), pp. 1-11, 2002.
Mitchell et al., J. Biol. Chem., vol. 283, No. 41, pp. 27345-27349, 2008.
Ogle et al., Annu. Rev. Biochem., vol. 74, pp. 129-177, 2005.
Ogle et al., Cell, vol. 111, No. 5, pp. 721-732, 2002.
Ogle et al., Science, vol. 292, No. 5518, pp. 897-902, 2001.
Rodnina et al., Annu. Rev. Biochem., vol. 70, pp. 415-435, 2001.
Saini et al., Genes Dev., vol. 24, No. 1, pp. 97-110, 2010.
Shabalina et al., Nucleic Acids Res., vol. 32, No. 5, pp. 1774-1782, 2004.
Short et al., J. Biol. Chem., vol. 277, pp. 32697-32705, 2002.
Sonenberg et al., *Cell*, vol. 136, No. 4, pp. 731-745, 2009.
Touriol et al., Biol. Cell, vol. 95, pp. 169-178, 2003.
Valasek et al., *Mol. Cell. Biol.*, vol. 24, No. 21, pp. 9437-9455; 2004.
Welch et al., *Nature*, vol. 447, No. 7140, pp. 87-91, 2007.
Winzeler et al., *Science*, vol. 285, No. 5429, pp. 901-906, 1999.
Wu et al., Methods Enzymol., vol. 429, pp. 203-225, 2007.
Yoon et al., *Mol. Cell. Biol.*, vol. 12, No. 1, pp. 248-260, 1992.
Zhang et al., *J. Biomol. Screen.*, vol. 4, No. 2, pp. 67-73, 1999.
Zitomer et al., *Mol. Cell Biol.*, vol. 4, No. 7, pp. 1191-1197, 1984.

* cited by examiner

*Primary Examiner* — Rei-tsang Shiao
(74) *Attorney, Agent, or Firm* — Venable LLP; Keith G. Haddaway; Annette K. Kwok

(57) ABSTRACT

A screening method for identifying compounds that alter the fidelity with which the initiation codon in mRNAs is recognized by the translational apparatus in eukaryotes is disclosed. This screening method was used to identify compounds having such activity. Methods of altering the fidelity of initiation codon selection are also disclosed. Methods of treating disorders characterized by single nucleotide mutations in initiation codons using compounds identified by the screening method, as well as methods of treating fungal and parasitic infections and hyperproliferative disorders using compounds identified by the screening method are also disclosed.

19 Claims, 20 Drawing Sheets

| Fxxx(mut)/Fxxx(wt) | eIF1 D83G | eIF1 scG107S | eIF1 scG107K | eIF1 sc93-97 | eIF1A hc – 107-153 | EIF1A hc – 124-153 | eIF2 SUI3-2 (F252 background) | eIF5 G31R (F252 background) |
|---|---|---|---|---|---|---|---|---|
| cug | 10.3 | 4.2 | 5.7 | 7.7 | 8.0 | 9.3 | 5.9 | 1.2 |
| gug | 17.7 | 4.6 | 5.5 | 7.6 | 11.1 | 13.6 | 7.9 | 1.4 |
| uug | 17.3 | 3.9 | 6.0 | 6.6 | 9.9 | 11.4 | 7.2 | 12.6 |
| aag | | | | | | | | |
| acg | 6.0 | 8.2 | 10.9 | 4.7 | 7.1 | 11.8 | 3.4 | 0.8 |
| agg | | | | | | | | |
| aua | 8.7 | 6.5 | 9.0 | 8.3 | 10.0 | 10.6 | 5.8 | 0.8 |
| auc | 9.8 | 5.1 | 8.5 | ~5.4 | 12.9 | 15.0 | 5.5 | 0.7 |
| auu | 1.5 | 3.3 | 5.9 | 2.5 | 4.5 | 5.6 | 1.3 | 0.2 |

Figure 10

IDENTIFICATION AND USE OF COMPOUNDS THAT AFFECT THE FIDELITY OF EUKARYOTIC TRANSLATION INITIATION CODON SELECTION

CROSS-REFERENCE TO RELATED APPLICATION

This application claims priority to U.S. Provisional Application No. 61/315,240 filed Mar. 18, 2010, the entire contents of which are hereby incorporated by reference.

This invention was made with United States Government support under R21 DK078633 awarded by the National Institutes of Health. The United States Government has certain rights in the invention.

SEQUENCE LISTING

The instant application contains a Sequence Listing which has been submitted in ASCII format via EFS-Web and is hereby incorporated by reference in its entirety. Said ASCII copy, created on Mar. 17, 2011, is named 22431922.txt and is 2,193 bytes in size.

BACKGROUND

1. Field of the Invention

The present invention relates to compounds that affect the fidelity of eukaryotic translation initiation codon selection and screening methods for identifying such compounds.

2. Background of the Invention

Translation of mRNA into functional protein is energetically expensive and must be highly accurate. The initiation phase of protein synthesis establishes the reading frame of translation and commits the cellular machinery to begin the elongation phase. For most mRNAs, the start codon is an AUG. It has been shown that codons that vary from AUG in one position (near-cognates) can be used up to ~8% as efficiently as AUG codons as start sites in *S. cerevisiae* (Zitomer et al., *Mol. Cell. Biol.*, vol. 4, no. 7, pp. 1191-1197, 1984; Clements et al., *Mol. Cell. Biol.*, vol. 8, no. 10, pp. 4533-4536, 1988; Donahue et al., *Mol. Cell. Biol.*, vol. 8, no. 7, pp. 2955-2963, 1988; Kolitz et al., *RNA*, vol. 15, no. 1, pp. 138-152, 2009). Translation initiation at non-AUG codons has been shown to occur naturally in both mammals and yeast. For example, CAPC, a protein over-expressed in some cancers, initiates translation using a non-AUG start codon (Anaganti et al. 2009). In yeast, two tRNA synthetase genes, GRS1 and ALA1, use non-AUG start codons for normal translation (UUG and ACG, respectively) (Chang and Wang 2004; Tang et al. 2004). Additionally, using ribosomal profiling Ingolia et al. (2009) identified 143 actively translated upstream open reading frames (uORFs) that appear to have non-AUG start codons in yeast. Interestingly, translation from these small uORFs is increased upon amino acid starvation, although neither the reason for this effect nor its mechanism is yet understood (Ingolia et al. 2009).

Recent studies using a reconstituted *S. cerevisiae* translation initiation system have elucidated core events involved in start codon selection. Briefly, the 40S subunit with eukaryotic initiation factor (eIF) 1, eIF1A, the ternary complex (TC: eIF2, initiator methionyl-tRNA and GTP) and eIF5 (the GTPase activating protein (GAP) for eIF2) is loaded onto the 5' end of the mRNA and scans to locate the start codon. In vivo, eIF4F, eIF4B and eIF3 are involved in loading of this 43S ribosomal pre-initiation complex (PIC) onto the 5' end of the mRNA and subsequent scanning of the message. After the initiator tRNA anti-codon base pairs with the mRNA start codon, eIF1 is released from the complex. Loss of eIF1 in turn allows inorganic phosphate to be released from eIF2, converting the factor into its GDP-bound form. The release of eIF1 also produces a conformational change in the complex that is thought to prevent further scanning. At this stage, the large ribosomal subunit joins the small ribosomal complex with the help of eIF1A and eIF5B, producing an 80S initiation complex that can enter the elongation phase of the cycle (for reviews of the mechanism of eukaryotic translation initiation see (Lorsch et al., *J. Biol. Chem.*, vol. 285, no. 21203-21207, 2010; Sonenberg et al., *Cell*, vol. 136, no. 4, pp. 731-745, 2009; (Jackson et al., *Nat. Rev. Mol. Cell. Biol.*, vol. 11, no. 2, pp. 113-127, 2010).

Although many steps involved in locating the start codon have been elucidated, the mechanistic details of this process are still a mystery. Many components of the translation machinery are known to impact the fidelity of start codon selection. Mutations in eIF1 (Yoon et al., *Mol. Cell. Biol.*, vol. 12, no. 1, pp. 248-260, 1992), 1A (Fekete et al., *EMBO J.*, vol. 24, no. 20, pp. 3588-3601, 2005; Saini et al., *Genes Dev.*, vol. 24, no. 1, pp. 97-110, 2010), eIF2 (Donahue et al., *Cell*, vol. 54, no. 5, pp. 621-632, 1988; Castilho-Valavicius et al., *Genetics*, vol. 124, no. 3, pp. 483-495, 1988), eIF5 (Huang et al., *Genes Dev.*, vol. 11, no. 18, pp. 2396-2413, 1997), eIF3 (Valasek et al., *Mol. Cell. Biol.*, vol. 24, no. 21, pp. 9437-9455; 2004) and eIF4G (He et al., *Mol. Cell. Biol.*, vol. 23, no. 15, pp. 5431-5445, 2003) are known to decrease the fidelity of start codon selection in vivo (Sui⁻ phenotype), and have been important tools to study the steps involved in translation initiation. While mechanistically very different, the selection of the start codon in the P-site during translation initiation can be related to selection of tRNA in the A-site during elongation; both processes are dependent on matching codon:anticodon base pairing, which triggers downstream events (Kolitz et al., *RNA*, vol. 15, no. 1, pp. 138-152, 2009; Cigan et al., *Science*, vol. 242, no. 4875, pp. 93-97, 1988; Ogle et al., *Science*, vol. 292, no. 5518, pp. 897-902, 2001). Small molecules such as the aminoglycoside family of antibiotics have been crucial tools to probe the mechanism of tRNA selection in the ribosomal A-site during the elongation phase of translation (Rodnina et al., *Annu. Rev. Biochem.*, vol. 70, pp. 415-435, 2001; Ogle et al., *Cell*, vol. 111, no. 5, pp. 721-732, 2002; Ogle et al., *Annu. Rev. Biochem.*, vol. 74, pp. 129-177, 2005). Although mutations in eukaryotic initiation factors have been studied, no chemical modulators of start codon selection exist to help elucidate the mechanism of this complicated process. Compounds that increase or decrease misreading during initiation could provide unique insight to how AUG is selected during initiation.

SUMMARY

Embodiments of the invention include methods of altering the fidelity of eukaryotic translation initiation codon selection by administering to a cell a compound of Formula I-V:

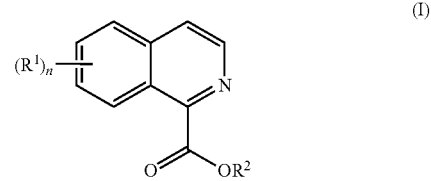

where n is an integer from 1 to 4; $R^1$ is H, halogen, alkyl, $NO_2OR^3$, $N(R^4)_2$, or $SR^5$; $R^2$ is H or alkyl; $R^3$ is H or alkyl, and $R^4$ is H or alkyl and $R^5$ is H or alkyl;

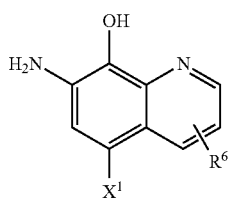

where $X^1$ is Br, or I; $R^6$ is H, halogen, alkyl, $NO_2$, $OR^3$, $N(R^4)_2$, or $SR^5$; $R^3$ is H or alkyl, and $R^4$ is H or alkyl and $R^5$ is H or alkyl;

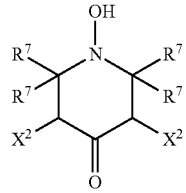

where $X^2$ is F, Cl, Br, or I; $R^7$ is H or alkyl;

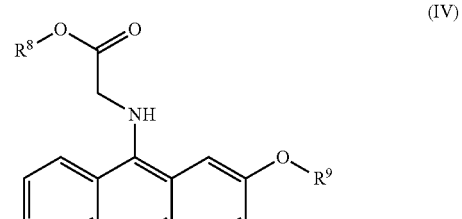

where $X^3$ is F, Cl, Br, or I; $R^8$ is H or alkyl; $R^9$ is H or alkyl;

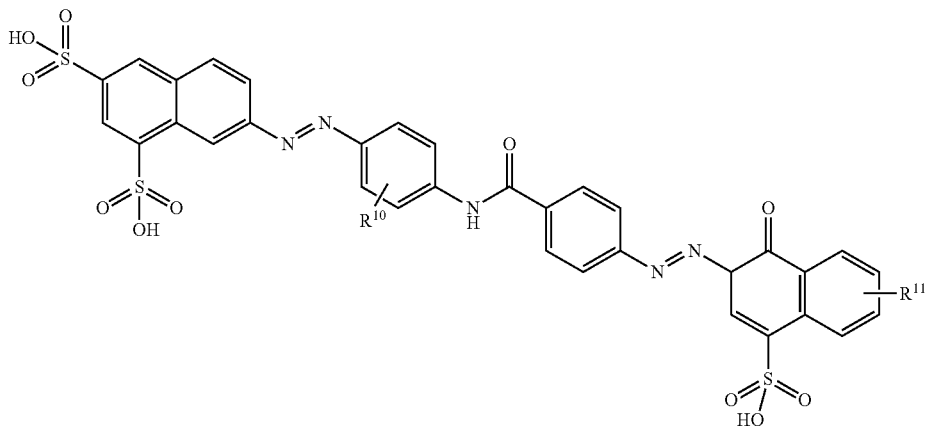

where $R^{10}$ is H or alkyl and $R^{11}$ is H or alkyl; and pharmaceutically acceptable salts thereof.

Some embodiments include methods of altering the fidelity of eukaryotic translation initiation codon selection by administering to a cell a compound of Formula (I) or (II).

In some embodiments, the compound may be one of the compounds shown below.

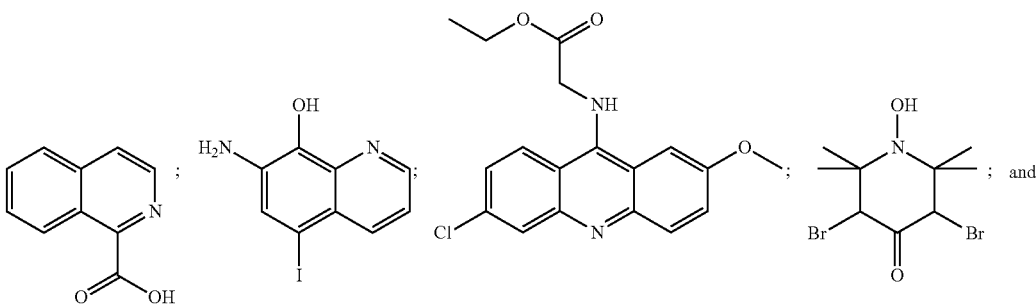

-continued

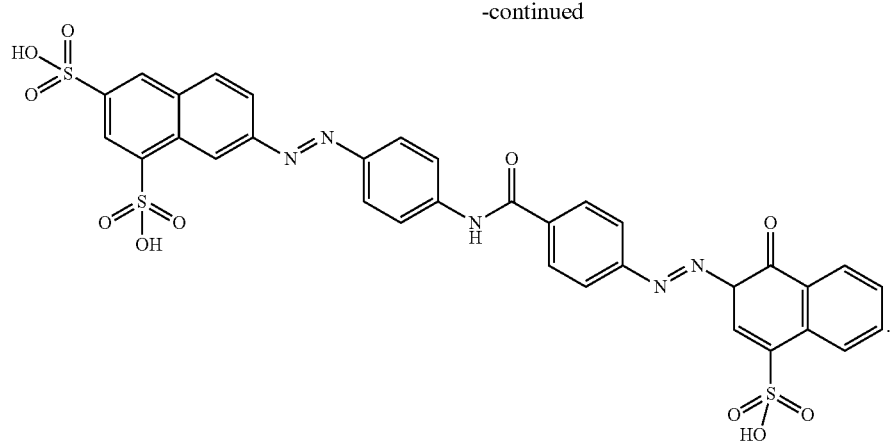

In some embodiments, the compound may be one of the compounds shown below.

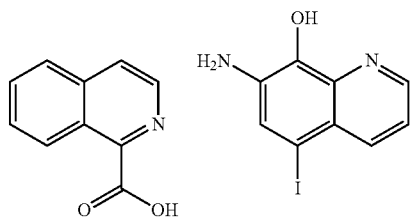 [SMILES: O=C(O)c1nccc2ccccc12 ; Nc1cc(I)c2cccnc2c1O]

Embodiments of the invention include methods for screening a test compound by introducing the test compound to eukaryotic cells in a culture where the cells have a DNA sequence encoding a first reporter protein, and where the mRNA from the first reporter protein has an initiation codon that is a near-cognate of AUG. Then measuring the change in the amount of reporter protein. In some embodiments the cells also have a DNA sequence encoding a second reporter protein, where the mRNA from the second reporter protein has an AUG initiation codon.

In embodiments, the step of measuring the amount of reporter protein also includes measuring the ratio between the amount of first reporter protein and the second reporter protein.

In some embodiments, the eukaryotic cells are yeast cells. In some embodiments, the eukaryotic cells are mammalian cells.

In some embodiments, the first reporter protein is a luciferase protein. In some embodiments, the first reporter protein is a firefly luciferase protein.

In some embodiments having a second reporter protein, the second reporter protein is a luciferase protein. In some embodiments, the second reporter protein is a *Renilla* luciferase protein.

In some embodiments, the cells have a first and second reporter protein and the first reporter protein is a firefly luciferase protein and the second reporter is a *Renilla* luciferase protein.

Embodiments of the invention include methods of treating a disorder comprising administering to a subject in need of treatment an effective amount of a compound of formula I-V, shown below.

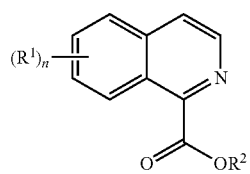

where n is an integer from 1 to 4; $R^1$ is H, halogen, alkyl, $NO_2OR^3$, $N(R^4)_2$, or $SR^5$; $R^2$ is H or alkyl; $R^3$ is H or alkyl, and $R^4$ is H or alkyl and $R^5$ is H or alkyl;

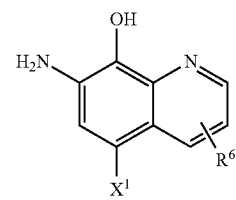

where $X^1$ is Br, or I; $R^6$ is H, halogen, alkyl, $NO_2$, $OR^3$, $N(R^4)_2$, or $SR^5$; $R^3$ is H or alkyl, and $R^4$ is H or alkyl and $R^5$ is H or alkyl;

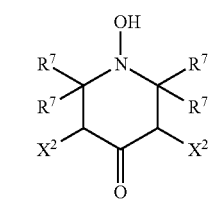

where $X^2$ is F, Cl, Br, or I; $R^7$ is H or alkyl;

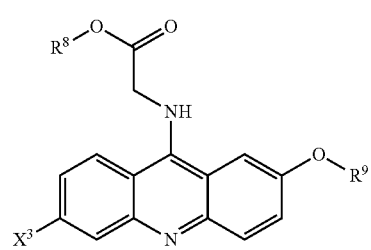

where $X^3$ is F, Cl, Br, or I; $R^8$ is H or alkyl; $R^9$ is H or alkyl; and

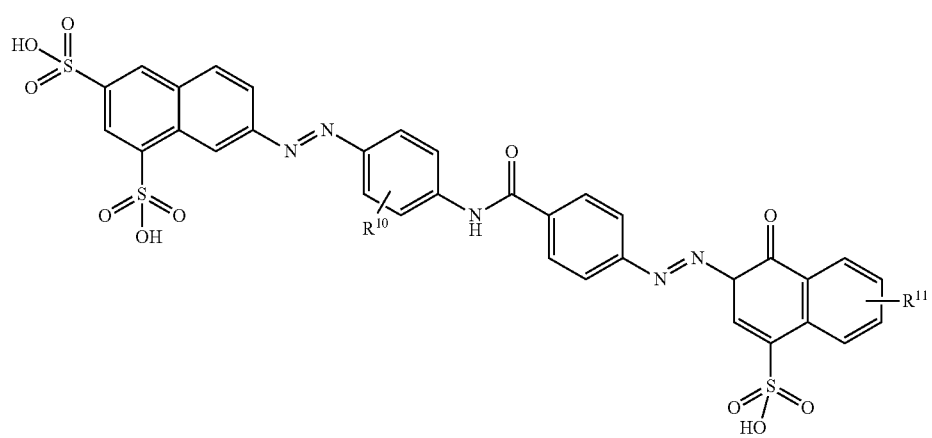

(V)

or pharmaceutically acceptable salt thereof. The disorder is: a disorder characterized by a non-AUG initiation codon, a fungal infection, a parasitic infection, or a hyperproliferative disorder.

In some treatment methods, the compound is a compound of Formula (I) or (II).

In some treatment methods, the compound is one of the compounds shown below.

In some embodiments where the disorder is a genetic disorder characterized by a single nucleotide mutation in the initiation codon, the disorder may be, for example, beta-thalassemia, alpha-thalassemia, hemoglobin H disease, phenylketonuria, congenital adrenal hyperplasia, Smith-Lemli-Opitz Syndrome, Refsum disease, Laron syndrome (LS) or growth hormone (GH) insensitivity syndrome (GHIS), cerebral adrenoleukodystrophy (ALD) and adrenomyeloneur-

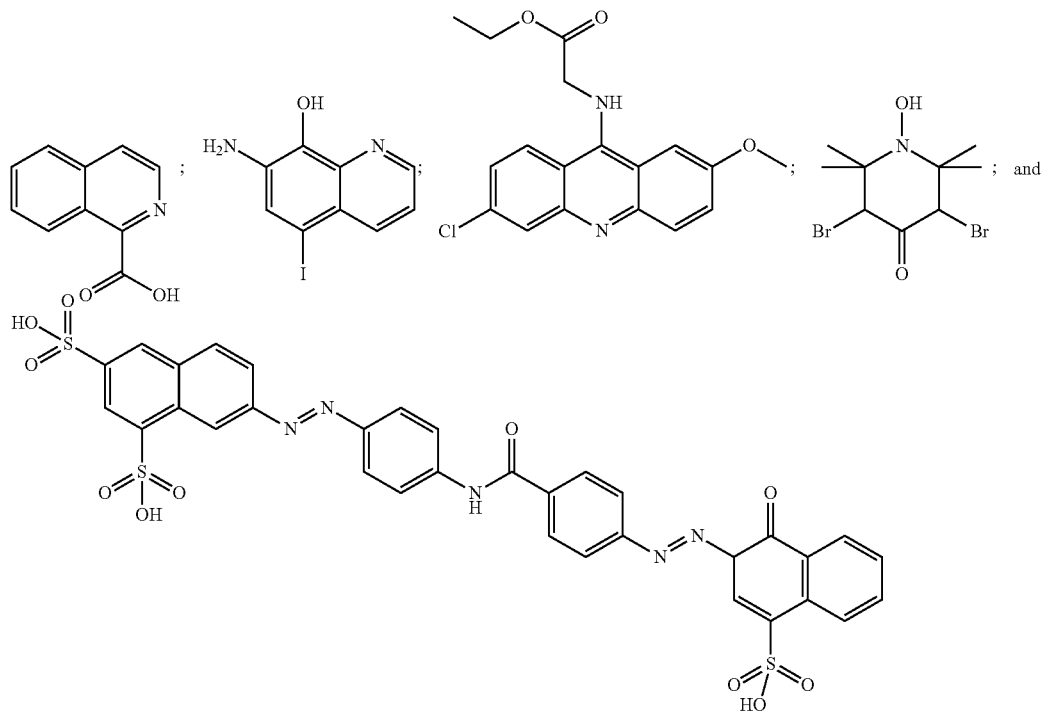

In some treatment methods, the compound is one of the compounds shown below.

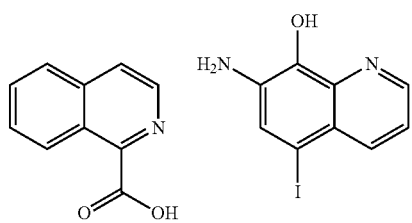 [SMILES: O=C(O)c1nccc2ccccc12 ; Nc1cc(I)c2cccnc2c1O]

opathy (AMN), Ataxia, Combined factor V-factor VIII deficiency (F5F8D), melanoma, Rhmod syndrome, glycogen storage disease type V (McArdle's disease), Autosomal dominant neurohypophyseal diabetes insipidus (ADNDI), Norrie disease (ND), Leukocyte adhesion deficiency (LAD), Niemann Pick disease (NPD), mucopolysaccharidosis type I (MPS) or Hurler/Scheie syndrome (IH/S), Tay-Sachs disease, or hyperphenylalaninemia.

In some embodiments, the disorder is a fungal infection. In some embodiments, the disorder is a parasitic infection. In some embodiments, the disorder is a hyperproliferative disorder.

In some embodiments, the presently disclosed screening method uses a dual luciferase assay in which renilla and firefly luciferase are expressed from the same plasmid, but as separate messages. Renilla (Rluc) luciferase mRNA, with an AUG start codon, acts as an internal control for expression of firefly (Fluc) luciferase mRNA, with the near cognate codon UUG. Screening of over 50,000 compounds identified compounds that increase expression from UUG relative to AUG.

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

FIG. 2A shows a schematic of the coding region of the plasmid used for the dual luciferase assay. P, promoter; T, terminator. The ADH promoter and HIS terminator were used to produce renilla luciferase mRNA, and the GPD promoter and CYC terminator were used for firefly luciferase mRNA. FIG. 2B shows a flow-chart for identifying compounds that alter the fidelity of start codon recognition.

FIG. 3A shows increasing volumes of yeast (strain BY4741) culture expressing FlucUUG (circles) and RlucAUG (squares) from plasmid pFuugRaug were added to lysis buffer, and the resulting luciferase activities measured. Points are fit to a straight line with R>0.99 for both renilla and firefly luciferase activities. FIG. 3B shows the effect of DMSO on the Fluc/Rluc ratio for AUG/AUG (white bars) and UUG/AUG (filled bars). BY4741 with pFuugRaug or pFaugRaug were grown with 3% DMSO under screening conditions. The effect of DMSO on the ratio was controlled for by normalization with the DMSO-only control during the screening analysis.

FIG. 4A shows BY4741 transformed with pFuugRaug grown with various concentrations of cycloheximide and the luciferase activities measured after four hours (circles are FlucUUG, squares are RlucAUG). FIG. 4B shows BY4741 with pFuugRaug, as above, as well as with pFaugRaug, grown with cycloheximide and the UUG/AUG (squares) and AUG/AUG (circles) ratios were measured. The Fluc/Rluc ratio of the solvent-only control was used to normalize the treated samples so that both ratios (UUG/AUG and AUG/AUG) equal 1 in the absence of drug.

FIG. 7A shows BY4741 expressing Fluc with either an AUG or UUG start codon treated with various concentrations of NSC218351, and normalized to the internal Rluc control with an AUG start codon. The Fluc/Rluc ratio from each sample was then normalized to the appropriate DMSO-only control, so that each ratio equals 1 in the absence of compound (normalized FlucUUG, circles; normalized FlucAUG, squares). Points are the averages of at least 7 independent experiments ±standard error. FIG. 7B shows raw luciferase activity values with increasing concentrations of NSC218351. Symbols indicate luciferase values from pFuugRaug plasmid, and luciferase values from pFaugRaug counter-screening plasmid (Fluc, squares; Rluc, circles). Luciferase activities are normalized to the DMSO control values in each experiment, and the normalized values of at least 6 independent experiments are averaged (±average deviation).

FIG. 8A shows BY4741 expressing Fluc with either an AUG or UUG start codon treated with various concentrations of NSC92218, and normalized to the internal Rluc control with an AUG start codon. The Fluc/Rluc ratio from each sample was then normalized to the appropriate DMSO-only control, so that each ratio equals 1 in the absence of compound (normalized FlucUUG, circles; normalized FlucAUG, squares). Points are the averages of at least 7 independent experiments ±standard error. FIG. 8B shows raw luciferase activity values with increasing concentrations of NSC92218. Symbols indicate luciferase values from pFuugRaug plasmid, and luciferase values from pFaugRaug counter-screening plasmid (Fluc, squares; Rluc, circles). Luciferase activities are normalized to the DMSO control values in each experiment, and the normalized values of at least 6 independent experiments are averaged (±average deviation).

FIG. 9A shows Fluc expression from reporters with different near-cognate start codons in cells treated with NSC218351 (the black X is AUG). FIG. 9B shows Fluc expression from reporters with different near-cognate start codons in cells treated with NSC92218 (the black X is AUG).

FIG. 10 shows the effect of Sui⁻ mutants on all near-cognate start codons in the dual luciferase assay. The FlucXXX/FlucAUG ratio was measured for several Sui⁻ mutants, where XXX is the start codon that varies from AUG by one base pair. This ratio was normalized to the same ratio in the wild type control [(Fxxx/Faug)$_{Sui}$/(Fxxx/Faug)$_{wt}$] to illustrate the magnitude of the effect of the Sui⁻ mutations on initiation at each codon relative to a wild type strain.

FIG. 19A shows the FlucUUG/RlucAUG expression ratio and FIG. 19B shows the FlucAUG/RlucAUG expression ratio, in the presence of DMSO (white bars) or compounds (NSC218351, grey bars; NSC92218, black bars), measured in strain H3984 (hc eIF1) and compared to wild type (BY4741), and haplo-insufficient diploids for eIFs 1 (+/sui1Δ), 1A (+/tif11Δ) and 5 (+/tif5Δ) and compared to diploid wild type BY4743 (+/+). H3984 data are an average of 2 independent experiments. Error bars represent average deviation. The concentration of NSC218351 was 60 μM, and NSC92218 was 3.8 μM. Haplo-insufficiency results are averages of data from 2 separate transformants. The concentration of NSC218351 was 33 μM, and NSC92218 was 7 μM. FlucAUG/RlucAUG expression ratio with DMSO alone was used to normalize the Fluc/Rluc ratio for both FlucAUG and FlucUUG for each strain (normalized FlucAUG/RlucAUG with DMSO alone is 1 for each strain).

DETAILED DESCRIPTION

Figure 1:
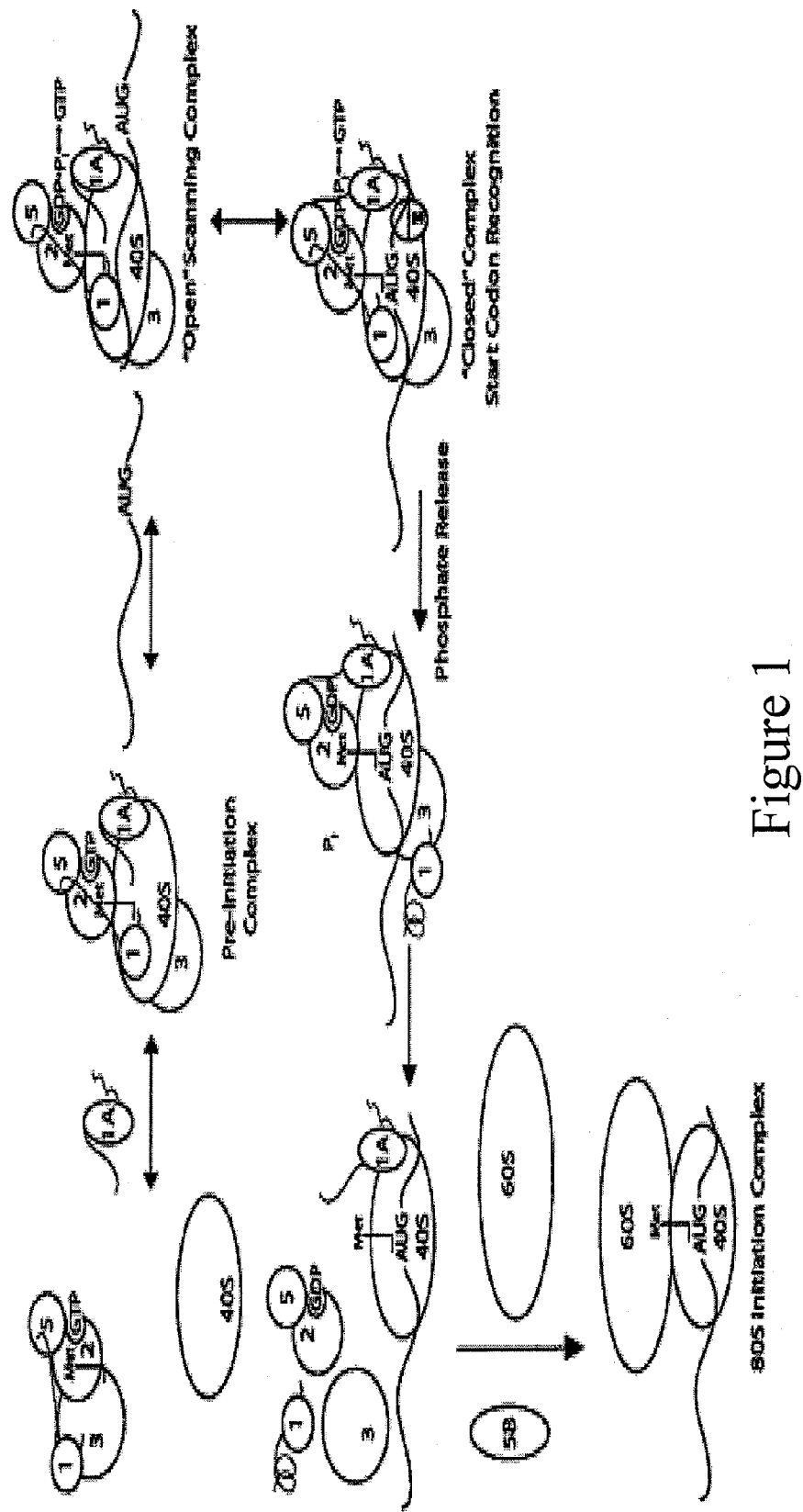
FIG. 1 is a model of eukaryotic translation initiation, excluding mRNA cap and poly(A) tail associated factors (Mitchell et al., J. Biol. Chem., vol. 283, no. 41, pp. 27345-27349, 2008). eIF2 delivers the Met-tRNAi to the 40S subunit, and converts GTP to GDP in response to identification of the start codon. eIF5 is the GAP for eIF2. The N and C termini of eIF1 and eIF1A have been shown to be critical in monitoring the identification of the start codon.

The presently disclosed subject matter now will be described more fully hereinafter with reference to the accompanying Drawings, in which some, but not all embodiments of the inventions are shown. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

DEFINITIONS

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

By "control" is meant a standard or reference condition.

By "disease" or "disorder" is meant any condition that damages or interferes with the normal function of a cell, tissue, organ or subject.

By "effective amount" is meant the amount of an agent required to ameliorate the symptoms of a disease relative to an untreated subject. The effective amount of an active therapeutic agent for the treatment of a disease or injury varies depending upon the manner of administration, the age, body weight, and general health of the subject. Ultimately, the attending clinician will decide the appropriate amount and dosage regimen.

By "modifies" is meant alters. An agent that modifies a cell, substrate, or cellular environment produces a biochemical alteration in a component (e.g., polypeptide, nucleotide, or molecular component) of the cell, substrate, or cellular environment.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

As used herein, a "prodrug" is a pharmacologically inactive compound that is converted into a pharmacologically active agent by a metabolic transformation.

By "subject" is meant a mammal, including, but not limited to, a human or non-human mammal, such as a rodent, bovine, equine, canine, ovine, or feline.

As used herein, the terms "treat," "treating," "treatment," "therapeutic" and the like refer to reducing or ameliorating a disorder and/or symptoms associated therewith. It will be appreciated that, although not precluded, treating a disorder or condition does not require that the disorder, condition or symptoms associated therewith be completely eliminated.

Chemical Terminology

While the following terms in relation to compounds found throughout this application are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like. Where multiple R groups are labeled with the same variable, e.g. where there are two or more $R^1$ groups in a molecule, each may be the same or different from other similarly labeled groups.

A named "R" or group will generally have the structure that is recognized in the art as corresponding to a group having that name, unless specified otherwise herein. For the purposes of illustration, certain representative "R" groups as set forth above are defined below.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. In exemplary embodiments, alkyl is limited to lower alkyl.

"Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

The terms "halo", "halide", or "halogen" as used herein refer to fluoro, chloro, bromo, and iodo groups.

The term "nitro" refers to the —$NO_2$ group.

Throughout the specification and claims, a given chemical formula or name shall encompass all tautomers, congeners, and optical- and stereoisomers, as well as racemic mixtures where such isomers and mixtures exist.

Description

Selection of the AUG start codon in eukaryotic translation initiation is a complex process (FIG. 1). The mechanisms underlying AUG recognition are not well understood, and the in vivo fidelity has not been well established. An in vivo dual luciferase assay can be used to measure the fidelity of initiation from near-cognate start codons in Saccharomyces cerevisiae (S. cerevisiae). The dual luciferase assay can be adapted to screen for compounds that alter the fidelity of translation initiation. Such compounds potentially may be powerful tools to investigate the mechanism of start codon selection in vivo and in in vitro systems including the reconstituted S. cerevisiae translation initiation system, and also would provide leads for drug development to treat diseases caused by altered translation initiation. Also, the dual luciferase assay and the reconstituted translation initiation system can be used to study the role of the consensus sequence surrounding initiation codons in yeast.

Many of the molecular steps leading to the selection of the AUG start codon in eukaryotic translation initiation have been elucidated using in vitro and in vivo systems, but the process is still not fully understood. Studies of tRNA selection during the elongation phase of prokaryotic translation have benefited from the use of small molecules. No such chemical tools exist, however, to probe start codon recognition in eukaryotic translation initiation and no compounds are currently known that modulate, e.g., alter, the fidelity of recognition of the translation initiation codon in eukaryotes. In fact, only a few compounds are known at all that specifically target any aspect of the process of protein synthesis in eukaryotes.

Compounds capable of modulating the fidelity of recognition of the translation initiation codon in eukaryotes would be useful for studying the mechanism of translation and could potentially be developed into drugs to treat a variety of diseases. For example, variants of many genetic diseases are known that are caused by mutations of the initiation codon. Compounds that reduce the fidelity of initiation codon recognition could ameliorate these diseases by allowing synthesis of the protein from the mutant mRNAs. In addition, compounds that alter the fidelity of initiation codon recognition might have antiproliferation properties because rapidly dividing cells, e.g., cancers, require high levels of protein synthesis and might be selectively sensitive to increased production of miscoded proteins. Finally, compounds that selectively target yeast, but not mammalian translation, could serve as antifungal agents and compounds that selectively or preferentially affect parasitic organisms rather than their mammalian hosts could have antiparasitic activities.

Assay

Embodiments of the invention include methods of screening a test compound by introducing a test compound to eukaryotic cells in a culture wherein the cells comprise a DNA sequence encoding a first reporter protein. The mRNA from the first reporter protein has an initiation codon that is a near-cognate of AUG. Measuring the change in the amount of reporter protein allows the effects of the compounds on recognition of the initiation codon to be assessed.

As used herein, a "near-cognate" of AUG is a codon that differs from AUG by only one base (e.g. UUG, GUG, CUG, AUA, AUC, AUU, ACG, AAG, AGG). Near-cognates may be prepared, for example, by site-directed mutagenesis or other means of changing a single nucleotide in a nucleotide sequence.

In some embodiments, the DNA sequence is contained in a plasmid or vector within the cells. In other embodiments, the DNA sequence is integrated into the cell's genomic DNA. Often, a plasmid or vector containing the DNA sequence is inserted into an existing cell by transformation or transfection using standard procedures. After insertion, the plasmid or vector may integrate into the genomic DNA in the cells.

In principal, any type of eukaryotic cell type may be used, so long as the cells don't interfere with expression of the reporter protein. In some embodiments, the cells are yeast cells, such as, for example, *Saccharomyces cereviseae*. In some embodiments, the cells are mammalian cells, such as, for example, mouse cells, rat cells, or human cells, or cells of any mammalian subject described herein.

Any protein that can be quantified may be used as the reporter protein. In some embodiments, the reporter protein is a protein that is not native to the cells used in the assay. In some embodiments, the reporter protein is a light emitting protein, such as, for example, a luciferase enzyme, such as, for example firefly luciferase or *Renilla* luciferase, or fluorescent protein, such as, for example, green fluorescent protein, enhanced green fluorescent protein, blue fluorescent protein, cyan fluorescent protein, yellow fluorescent protein, red fluorescent protein, and variants thereof. In some embodiments, the reporter protein may be colorimetric, such as, for example LacZ. In some embodiments, the first reporter protein is a firefly luciferase protein.

The amount of reporter protein may be measured by any means of quantifying protein expression. In some embodiments, where the reporter protein emits light, the amount of protein may be quantified by measuring the amount of luminescence or fluorescence. In some embodiments, using colorimetric reporter proteins, the amount of protein may be quantified by measuring absorbance at a frequency or range of frequencies. In other embodiments, the reporter protein may be quantified immunogenically, for example by Western blotting or ELISA. In some embodiments the amount of expression may be quantified by the level of growth of the cells allowed on or in selective media, for example, medium lacking histidine.

Active compounds are determined by an increase or decrease in the amount of the reporter protein. Compounds that increase the amount of reporter protein decrease the fidelity of eukaryotic translation initiation codon selection by increasing the use of non-AUG initiation codons. Compounds that decrease the amount of reporter protein increase the fidelity of eukaryotic translation initiation codon selection by decreasing the use of non-AUG initiation codons.

In some embodiments, additional experiments may be used to normalize the results. For example, in some embodiments an internal control may be used to normalize the measurements by the number of cells, which reduces the variation between different experiments and allows for more accurate comparisons. Other methods may also be used to normalize the measurements based on the number of cells, such as, for example, measuring the number of cells by optical density.

In some embodiments, counterscreens or secondary assays may be used to exclude compounds having non-specific activity. For example, the counterscreen and secondary assays described below may be used.

The threshold for active compounds may be set arbitrarily, so long as the change in reporter protein expression is measurable, reproducible, and statistically significant. For example, active compounds may be identified as those that cause an increase or decrease of at least, for example, 1.5 fold, 2 fold, 2.5 fold or more. A 1.5 fold increase means that the amount of protein expressed in the presence of compound is 1.5 times the amount of protein expressed in the absence of compound. In other words the amount of reporter protein expression increases by 50% upon administration of the compound.

The number of cells in the culture should be sufficient to give a detectable level of expression of the reporter protein, and may be readily optimized by one of ordinary skill in the art. Likewise, the amount of compound used in the assay should be high enough to produce a detectable difference in expression of the reporter protein, if the compound is an active compound. Compounds that are toxic to the cells at the initial concentration may be measured at lower, non-toxic concentrations.

In some embodiments, the cell includes a DNA sequence encoding a second reporter protein, where the mRNA from the second reporter protein has an AUG initiation codon.

As above, the DNA sequence may be part of a plasmid, or may be integrated into the genomic DNA of the cell.

Any protein that may be quantified may be used as the second reporter protein, so long as it is different from the first reporter protein and the two proteins may be quantified individually. In some embodiments, the second reporter protein may be a luciferase protein, fluorescent protein or colorimetric protein. In some embodiments, the second reporter protein is a *Renilla* luciferase protein.

In some embodiments, the first reporter protein is a firefly luciferase, and the second reporter protein is a *Renilla* luciferase protein. The two luciferase proteins may be independently quantified by measuring light emission because *Renilla* luciferase cannot use the firefly luciferase substrate, and firefly luciferase requires magnesium ions to produce light emission as described in U.S. Pat. No. 6,171,809 incorporated by reference in its entirety. To quantify the two proteins individually, for example, firefly luciferase substrate and magnesium ions may be added to sample containing the two luciferase enzymes. The amount of light emission is produced only by firefly luciferase and may be quantified. *Renilla* luciferase substrate and EDTA may then be added to the sample containing the two luciferase enzymes. Because the magnesium ions are sequestered by EDTA, any light emission is produced only by *Renilla* luciferase, and may be quantified.

In some embodiments, the measuring step includes measuring the ratio between the amount of the first reporter protein and the amount of the second reporter protein. The ratio allows the screening assay to be normalized to the amount of cells in each assay. Thus, comparisons may be made between different screening experiments without the need for additional normalization procedures, such as cell counting or optical density measurements.

In some embodiments, the method further includes a counterscreen. The counterscreen may eliminate false positives for example, or compounds that act by a mechanism other than altering the fidelity of eukaryotic translation initiation codon selection. The counterscreen may include, for example, performing a separate assay using the same first reporter protein having an AUG initiation codon.

In some embodiments, the counterscreen includes an assay using the same first reporter protein and second reporter protein used in the initial screen, but where both reporter proteins have an AUG initiation codon.

Any cells or reporter proteins discussed previously may be used in the counterscreen. In some embodiments, in the counterscreen, the first reporter protein is firefly luciferase, and the second reporter protein is *Renilla* luciferase.

Additional assays may be used to confirm the activity of the compound as a compound that alters the fidelity of eukaryotic translation initiation codon selection. For example, a cell growth assay using a cell line with a single-nucleotide mutation in the initiation codon for a protein essential for growth may be used. An active compound that decreases the fidelity of translation initiation codon selection allows the use of non-AUG initiation codons. Therefore, an essential gene may be expressed, allowing the cells to grow. For example, cells with a single-nucleotide mutation in the HIS4 protein can not grow on media lacking histidine. However, an active compound may allow sufficient HIS4 protein to be expressed, allowing the mutated cells to grow on media lacking histidine.

Other assays may be used, such as, for example, RT-PCR, to show that the compounds do not affect mRNA abundance. Other assays may be used to confirm that mRNA stability is not altered. For example, the effect of the compounds with these reporters may be tested in strains in which nonsense-mediated decay is inoperative, such as, for example, upf1Δ.

Methods

Embodiments include methods of altering the fidelity of eukaryotic translation initiation codon selection by administering to a cell a compound of Formula I-V:

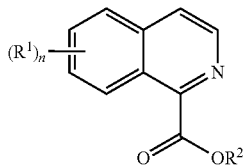
(I)

where n is an integer from 1 to 4; $R^1$ is H, halogen, alkyl, $NO_2OR^3$, $N(R^4)_2$, or $SR^S$; $R^2$ is H or alkyl; $R^3$ is H or alkyl, and $R^4$ is H or alkyl and $R^5$ is H or alkyl;

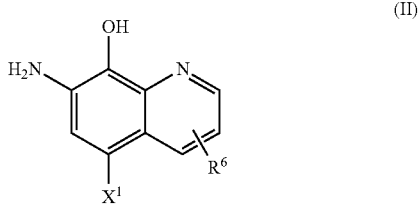
(II)

where $X^1$ is Br, or I; $R^6$ is H, halogen, alkyl, $NO_2$, $OR^3$, $N(R^4)_2$, or $SR^S$; $R^3$ is H or alkyl, and $R^4$ is H or alkyl and $R^5$ is H or alkyl;

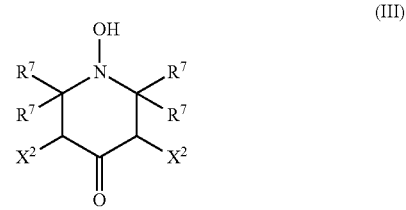
(III)

where $X^2$ is F, Cl, Br, or I; $R^7$ is H or alkyl;

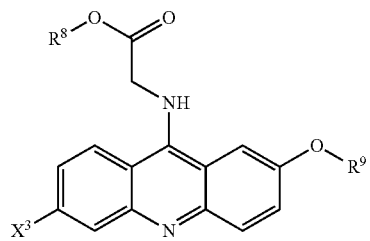
(IV)

where $X^3$ is F, Cl, Br, or I; $R^8$ is H or alkyl; $R^9$ is H or alkyl;

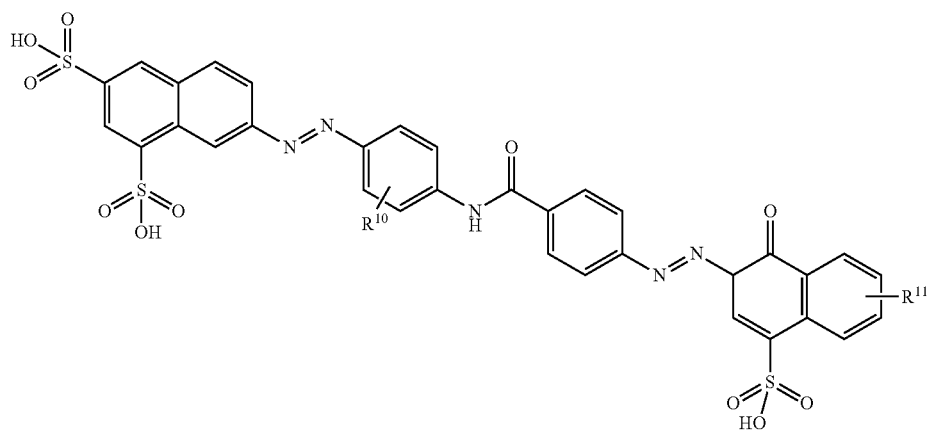
(V)

where $R^{10}$ is H or alkyl and $R^{11}$ is H or alkyl;
and pharmaceutically acceptable salts thereof.

In some embodiments, the compound is one shown below.

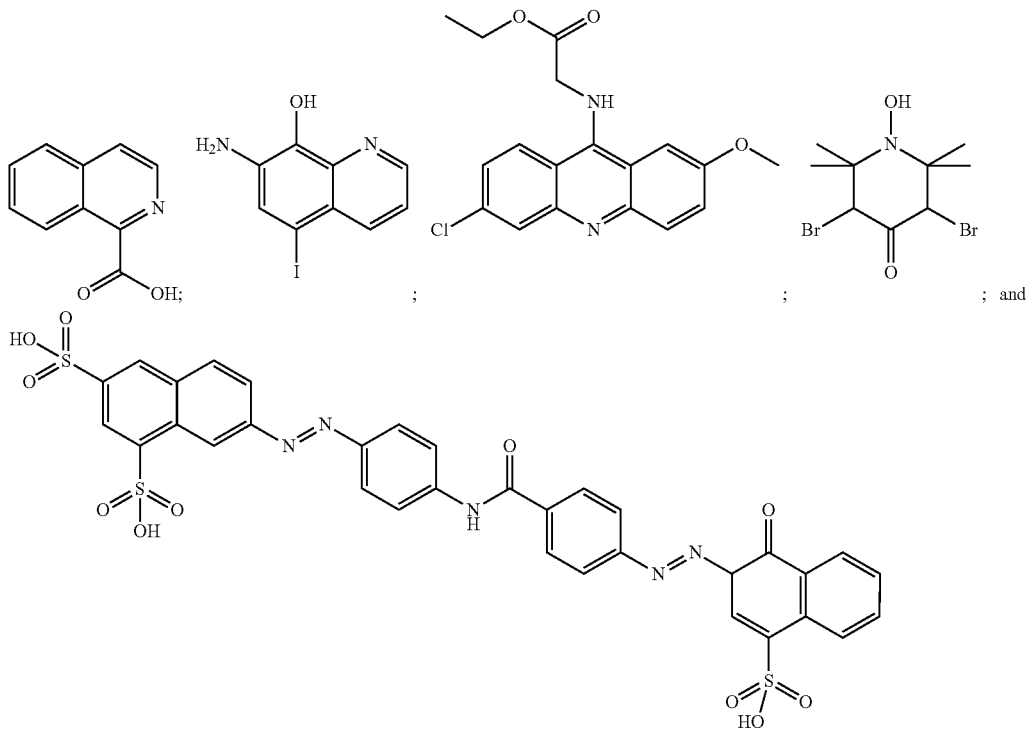

Altering the fidelity of eukaryotic translation initiation codon selection results in an increase or decrease in the amount of near-cognate (non-AUG) initiation codons used in protein translation. A compound that increases fidelity decreases the use of near-cognate (non-AUG) initiation codons for protein translation. A compound that decreases fidelity increases the use of near-cognate (non-AUG) initiation codons in protein translation. A sufficient amount of compound is administered to the cells to produce the desired change in fidelity.

In some embodiments, a compound may alter the fidelity of initiation codon selection on any mRNA expressed in the cell. In other words, a compound may have general activity. Alternatively, in some embodiments, a compound may alter the fidelity of initiation codon selection only on mRNAs expressed from a specific gene or specific group of genes. In other words, a compound may have specific activity. To achieve specific activity, a compound may alter the fidelity of initiation codon selection on mRNAs expressed from a specific gene or specific group of genes at a lower concentration than on mRNAs expressed from other genes.

The cells may be present in any medium, such as for example, in vitro (i.e. in culture medium), within a host (if a parasite), or in vivo (if a subject).

Methods of Treatment

The terms "treat" or "treating," and grammatical derivatives thereof, as used herein refer to any type of treatment that imparts a benefit to a subject afflicted with a disease or illness, including improvement in the condition of the subject (e.g., in one or more symptoms), delay in the progression of the condition, prevention or delay of the onset of the disease or illness, e.g., prophylactic treatment, enhancement of normal physiological functionality, and the like.

A "therapeutically effective amount" as provided herein refers to an amount of the presently disclosed compounds and/or compositions necessary to provide the desired therapeutic effect, e.g., an amount that is effective to prevent, alleviate, or ameliorate symptoms of disease or prolong the survival of the subject being treated. As would be appreciated by one of ordinary skill in the art upon review of the present disclosure, the exact amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

Embodiments include methods of treating a disorder by administering to a subject in need of treatment an effective amount of a compound selected from the group consisting of

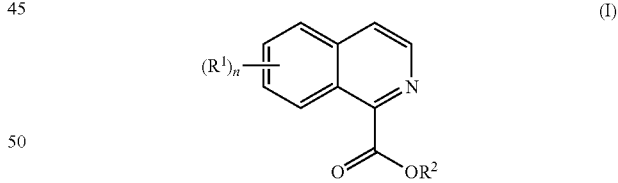

(I)

where n is an integer from 1 to 4; $R^1$ is H, halogen, alkyl, $NO_2OR^3$, $N(R^4)_2$, or $SR^5$; $R^2$ is H or alkyl; $R^3$ is H or alkyl, and $R^4$ is H or alkyl and $R^5$ is H or alkyl;

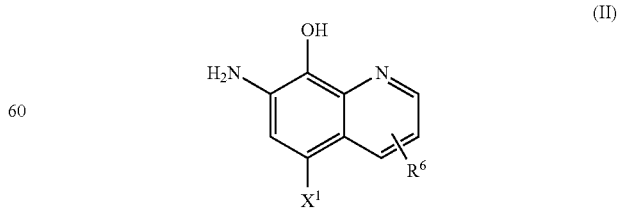

(II)

where $X^1$ is Br, or I; $R^6$ is H, halogen, alkyl, $NO_2$, $OR^3$, $N(R^4)_2$, or $SR^5$; $R^3$ is H or alkyl, and $R^4$ is H or alkyl and $R^5$ is H or alkyl;

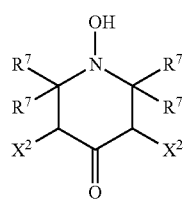

where $X^2$ is F, Cl, Br, or I; $R^7$ is H or alkyl;

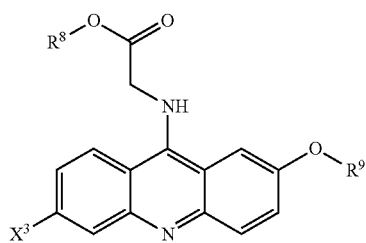

where $X^3$ is F, Cl, Br, or I; $R^8$ is H or alkyl; $R^9$ is H or alkyl; and

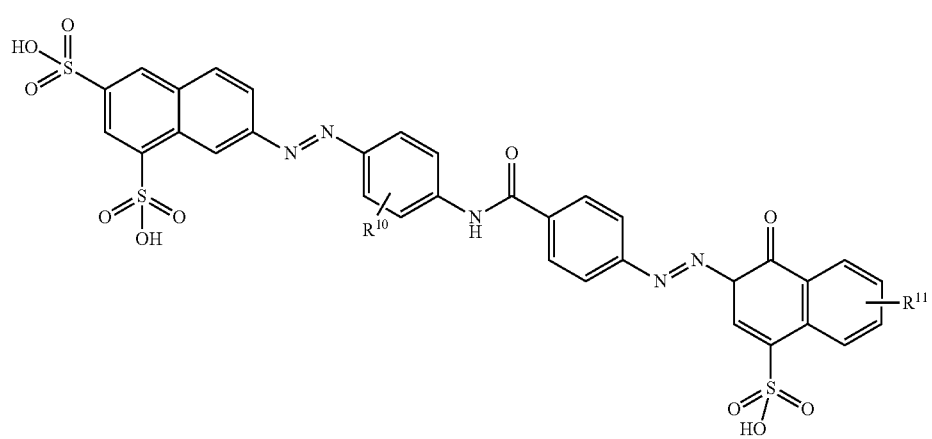

or pharmaceutically acceptable salt thereof.

In some embodiments, the disorder is: a disorder characterized by a non-AUG initiation codon, a fungal infection, a parasitic infection, or a hyperproliferative disorder. Disorders characterized by a non-AUG initiation codon may be, for example, a genetic disorder caused by a mutation in the initiation codon of a protein; use of non-AUG start codons in hyperproliferating cells to express different isoforms of oncoproteins; or use of non-AUG start codons in viruses to express viral proteins. As used herein, a 'disorder' is any condition that damages or interferes with the normal function of a cell, tissue, organ or subject, i.e. a disorder not present in wild-type cells, tissues, organs or subjects.

A number of known genetic disorders are characterized by a single nucleotide mutation in the initiation codon. Examples include, beta-thalassemia, alpha-thalassemia, hemoglobin H disease, phenylketonuria, congenital adrenal hyperplasia, Smith-Lemli-Opitz Syndrome, Refsum disease, Laron syndrome (LS) or growth hormone (GH) insensitivity syndrome (GHIS), cerebral adrenoleukodystrophy (ALD), adrenomyeloneuropathy (AMN), Ataxia, Combined factor V-factor VIII deficiency (F5F8D), melanoma, Rhmod syndrome, glycogen storage disease type V (McArdle's disease), Autosomal dominant neurohypophyseal diabetes insipidus (ADNDI), Norrie disease (ND), Leukocyte adhesion deficiency (LAD), Niemann Pick disease (NPD), mucopolysaccharidosis type I (MPS) or Hurler/Scheie syndrome (IH/S), Tay-Sachs disease, or hyperphenylalaninemia. In these disorders, administration of a compound that decreases the fidelity of eukaryotic translation initiation codon selection may allow sufficient protein to be produced to ameliorate the symptoms of the genetic disorder.

In some embodiments, the disorder may be a fungal infection or parasite infection, where the compounds are specific to fungal or parasitic protein translation. In such instances, the compounds act selectively, e.g. more effectively, predominately or only against the fungi cells, or parasite cells, and not against the host cells. Examples of eukaryotic parasites include, for example, *Plasmodium* (malaria), Trypanosomes, *Leishmania, Giardia, Nematodes, Trematodes, Cestoidea*, and Amoeba.

In other embodiments, the compound may be used against other organisms, such as insects, or mammals for pest or rodent control.

In other embodiments, the disorder may be a virus within mammalian cells, where the compound inhibits production of viral proteins that use non-AUG start codons (where the compound increases fidelity), or produces mis-translated viral proteins by increasing use of non-AUG start codons (where the compound decreases fidelity). The compounds may also act against a virus by disrupting the balance of translation from cognate and near-cognate codons required for maintaining the proper balance of viral gene products.

In some embodiments, the disorder may be a hyperproliferative disorder. High amounts of protein are produced in rapidly proliferating cells. Administration of a compound that decreases the fidelity of eukaryotic translation initiation codon selection may produce increased levels of protein mis-translation. In addition, the compounds may alter the balance of expression of short and long isoforms of oncoproteins and proteins involved in growth control generated by initiation of translation at alternative cognate and near-cognate initiation codons. Examples of oncoproteins and proteins involved in growth control with isoforms generated from alternative initiation codons include c-myc, VEGF, JunD, ornithine decarboxylase and C/EBP (Blackwood et al., Mol. Biol. Cell, vol.

5, pp. 597-609, 1994; Cencig et al., Oncogene, vol. 23, pp. 267-77, 2004; Bastide et al., Nucleic Acids Ress, vol. 36, pp. 2434-2445, 2008; Touriol et al., Biol. Cell, vol. 95, pp. 169-178, 2003; Ivanov et al., Proc. Natl. Acad. Sci. U.S.A., vol. 105, pp. 10079-10084, 2008; Short et al., J. Biol. Chem., vol. 277, pp. 32697-32705, 2002).

In some embodiments, the administered compound is one of the compounds shown below.

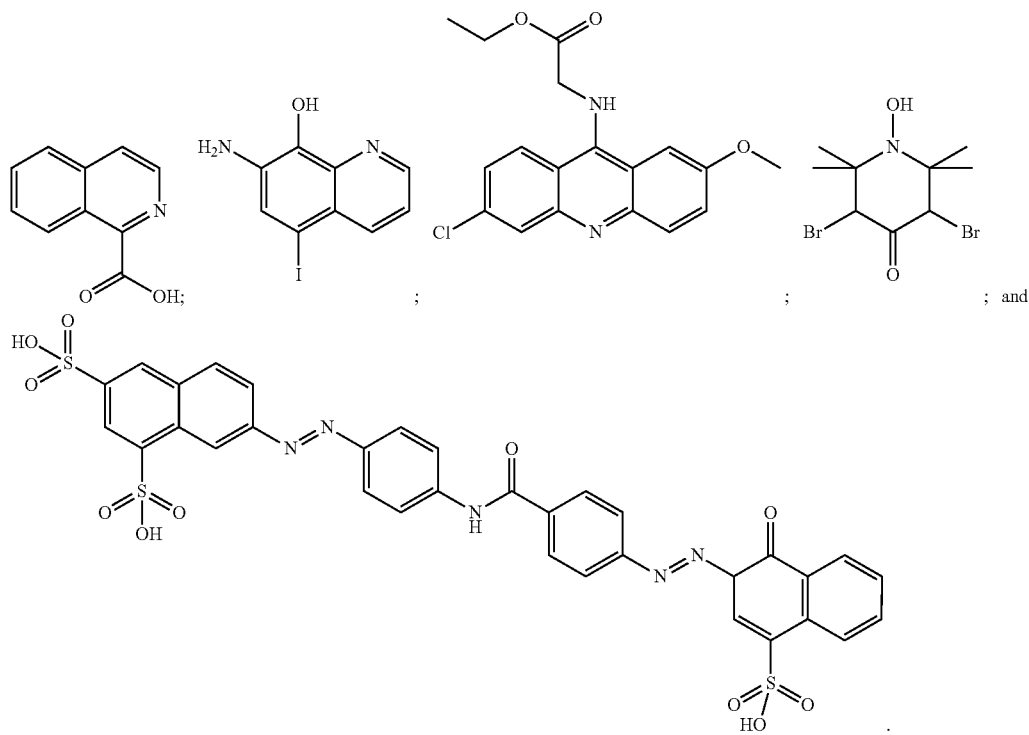

The presently disclosed compound(s) can be administered therapeutically to achieve a therapeutic benefit or prophylactically to achieve a prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a compound to a patient suffering from a condition provides therapeutic benefit not only when the underlying condition is eradicated or ameliorated, but also when the patient reports a decrease in the severity or duration of the symptoms associated with the condition. Therapeutic benefit also includes halting or slowing the progression of the disease, regardless of whether improvement is realized by the patient.

For prophylactic administration, the presently disclosed compound(s) and compositions can be administered to a subject at risk of developing a particular condition, e.g., heart failure, or at risk to the toxic side effects of cardiac glycosides. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an IC50 of the particular compound as measured in an in vitro assay known in the art. Calculating dosages to achieve such circulating blood or serum concentrations taking into account the bioavailability of the particular compound is well within the capabilities of skilled artisans. For guidance, see Fingl & Woodbury, "General Principles," In: Goodman and Gilman's The Pharmaceutical Basis of Therapeutics, Chapter 1, pp. 1-46, latest edition, Pagamonon Press, and the references cited therein.

Initial dosages also can be estimated from in vivo data, such as animal models. Animal models useful for testing the efficacy of compounds to treat or prevent the various diseases described above are well-known in the art. Dosage amounts will depend on, among other factors, the activity of the compound, its bioavailability, the mode of administration and various factors discussed above. Dosage amount and interval can be adjusted individually to provide levels of the compound(s) sufficient to maintain a therapeutic or prophylactic effect. Skilled artisans will be able to optimize effective local dosages without undue experimentation.

The presently disclosed compound(s) and compositions can be administered once per day, a few or several times per day, or even multiple times per day, depending upon, among other things, the indication being treated and the judgment of the prescribing physician.

Preferably, the presently disclosed compound(s) and compositions will provide therapeutic or prophylactic benefit without causing substantial toxicity. Toxicity of the compound(s) and compositions can be determined using standard pharmaceutical procedures. The dose ratio between toxic and therapeutic (or prophylactic) effect is the therapeutic index. Compounds(s) and compositions that exhibit high therapeutic indices are preferred.

Subject

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The subject also can refer to a cell or tissue sample.

Compounds

In all embodiments, active compounds may be present as pharmaceutically acceptable salts or other derivatives, such as ether derivatives, ester derivatives, acid derivatives, and aqueous solubility altering derivatives of the active compound. Derivatives include all individual enantiomers, diastereomers, racemates, and other isomers of the compounds. Derivatives also include all polymorphs and solvates, such as hydrates and those formed with organic solvents, of the compounds. Such isomers, polymorphs, and solvates may be prepared by methods known in the art, such as by regiospecific and/or enantioselective synthesis and resolution.

The ability to prepare salts depends on the acidity of basicity of the compounds. Suitable salts of the compounds include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts.

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compounds.

Pharmaceutical Compositions

Pharmaceutical compositions may include one or more active agent, i.e. a compound according to the invention, and may further contain other suitable substances and excipients, including but not limited to physiologically acceptable buffering agents, stabilizers (e.g. antioxidants), flavoring agents, agents to effect the solubilization of the compound, and the like.

In other embodiments, the pharmaceutical composition may be in any suitable form such as a solution, a suspension, an emulsion, an infusion device, or a delivery device for implantation or it may be presented as a dry powder to be reconstituted with water or another suitable vehicle before use. The composition may include suitable parenterally acceptable carriers and/or excipients.

In other embodiments, the pharmaceutical compositions may comprise an effective amount of an active agent in a physiologically-acceptable carrier. The carrier may take a wide variety of forms depending on the form of preparation desired for a particular route of administration. Suitable carriers and their formulation are described, for example, in Remington's Pharmaceutical Sciences by E. W. Martin.

In some embodiments, the active agent may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) or oral administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

In some embodiments, the pharmaceutical compositions may be in a form suitable for administration by sterile injection. In one example, to prepare such a composition, the compositions(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). For parenteral formulations, the carrier will usually comprise sterile water, though other ingredients, for example, ingredients that aid solubility or for preservation, may be included. Injectable solutions may also be prepared in which case appropriate stabilizing agents may be employed.

Formulations suitable for parenteral administration usually comprise a sterile aqueous preparation of the inhibitor, which may be isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery or localized delivery. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

In some embodiments, the pharmaceutical compositions may be in a form suitable for oral administration. In compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. If desired, tablets may be sugar coated or enteric coated by standard techniques.

Compositions suitable for oral administration may be presented as discrete units such as capsules, cachets, tablets, or lozenges, each containing a predetermined amount of the active ingredient as a powder or granules. Optionally, a suspension in an aqueous liquor or a non-aqueous liquid may be employed, such as a syrup, an elixir, an emulsion, or a draught. Formulations for oral use include tablets containing active ingredient(s) in a mixture with pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

A syrup may be made by adding the compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

In some embodiments, the pharmaceutical composition may be in a form of nasal or other mucosal spray formulations (e.g. inhalable forms). These formulations can include purified aqueous solutions of the active compounds with preservative agents and isotonic agents. Such formulations can be adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

In some embodiments, the pharmaceutical composition may be in a form suitable for rectal administration. These formulations may be presented as a suppository with a suitable carrier such as cocoa butter, hydrogenated fats, or hydrogenated fatty carboxylic acids.

In some embodiments, the pharmaceutical composition may be in a form suitable for transdermal administration. These formulations may be prepared, for example, by incorporating the active compound in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, pharmaceutical compositions of the invention may further include one or more accessory ingredient(s) selected from encapsulants, diluents, buffers, flavoring agents, binders, disintegrants, surface active agents, thickeners, lubricants, preservatives (including antioxidants), and the like.

In some embodiments, pharmaceutical compositions may be formulated for immediate release, sustained release, delayed-onset release or any other release profile known to one skilled in the art.

In some embodiments, the pharmaceutical composition may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in the central nervous system or cerebrospinal fluid; (v) formulations that allow for convenient dosing, such that doses are administered, for example, once every one or two weeks; and (vi) formulations that target the site of a pathology. For some applications, controlled release formulations obviate the need for frequent dosing to sustain activity at a medically advantageous level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the inhibitor is formulated with appropriate excipients into a pharmaceutical composition that, upon administration, releases the inhibitor in a controlled manner. Examples include single or multiple unit tablet or capsule compositions, oil solutions, suspensions, emulsions, microcapsules, microspheres, molecular complexes, nanoparticles, patches, and liposomes.

In some embodiments, the pharmaceutical composition may comprise a "vectorized" form, such as by encapsulation of the inhibitor in a liposome or other encapsulate medium, or by fixation of the inhibitor, e.g., by covalent bonding, chelation, or associative coordination, on a suitable biomolecule, such as those selected from proteins, lipoproteins, glycoproteins, and polysaccharides.

In some embodiments, the pharmaceutical composition can be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents. Alternatively, the inhibitor may be incorporated in biocompatible carriers, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly (caprolactone), poly(lactic acid), poly(glycolic acid) or poly (ortho esters) or combinations thereof).

Unless the context clearly indicates otherwise, pharmaceutical compositions of all embodiments can comprise various pharmaceutically acceptable salts, or other derivatives described previously.

The formulation and preparation of such compositions are well known to those skilled in the art of pharmaceutical formulation. Formulations can be found in Remington: The Science and Practice of Pharmacy.

The pharmaceutical compositions may be provided in unit dosage forms (e.g., in single-dose ampules), or in vials containing several doses and in which a suitable preservative may be added. A composition of the invention may be in any suitable form such as a solution, a suspension, an emulsion, an infusion device, or a delivery device for implantation or it may be presented as a dry powder to be reconstituted with water or another suitable vehicle before use. The composition may include suitable parenterally acceptable carriers and/or excipients.

Further, in some embodiments, compounds disclosed herein may be prepared as prodrugs. The term "prodrug" refers to a therapeutic agent that has been chemically derivatized such that, upon administration to a subject, the derivative is metabolized to yield the biologically-active therapeutic agent. Accordingly, upon administration to a recipient, a prodrug is capable of providing (directly or indirectly) a compound of the presently disclosed subject matter or an inhibitorily active metabolite or residue thereof. Prodrugs can increase the bioavailability of the presently disclosed compounds when such compounds are administered to a subject (e.g., by allowing an orally administered compound to be more readily absorbed into the blood) or can enhance delivery of the parent compound to a biological compartment (e.g., the brain or lymphatic system) relative to a metabolite species.

The presently disclosed active compounds or prodrugs thereof can be formulated in the pharmaceutical compositions per se, or in the form of a hydrate, solvate, N-oxide or pharmaceutically acceptable salt, as is known in the art. Typically, such salts are more soluble in aqueous solutions than the corresponding free acids and bases, but salts having lower solubility than the corresponding free acids and bases also can be formed.

Dosage

The administration of a compound may be by any suitable means that results in a concentration of the compound that, combined with other components, is effective in preventing, diagnosing, prognosing, ameliorating, reducing, or stabilizing a deficit or disorder.

Generally, the amount of administered agent of the invention will be empirically determined in accordance with information and protocols known in the art. Often the relevant amount will be such that the concentration of compound in the blood stream of the patient is about equal to or larger than the $IC_{50}$ or $K_i$ of the compound. Typically agents are administered in the range of about 10 to 1000 µg/kg of the recipient. Other additives may be included, such as stabilizers, bactericides, and anti-fungals. These additives are present in conventional amounts.

The amount of the compound/agent to be administered varies depending upon the manner of administration, the age and body weight of the subject/patient, and with the subject's symptoms and condition. A compound is generally administered at a dosage that best achieves medical goals with the fewest corresponding side effects.

Kits

The pharmaceutical compositions can, if desired, be presented in a pack or dispenser device (individually or collectively referred to as "a kit"), which can contain one or more unit dosage forms containing the active compound(s) and compositions. The kit can, for example, comprise metal or plastic foil, such as a blister pack. The kit can be accompanied by instructions for administration.

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The above disclosure generally describes exemplary embodiments of the present invention. The examples disclosed below are provided to illustrate the invention but not to limit its scope. Other variants of the invention will be readily apparent to one of ordinary skill in the art and are encompassed by the appended claims. All publications, databases, patents and patent applications disclosed herein are hereby incorporated by reference in their entirety.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Strains and Plasmids

TABLE 1

Genotypes of strains used in this study.

| Strain | Genotype | Source |
|---|---|---|
| BY4741 | MATa his3Δ1 leu2Δ0 met15Δ0 ura 3Δ0 | Open Biosystems |
| YRP1 | YPH499; MATa snq2Δpdr5Δerg6Δ | (Kung et al. 2005) |
| upf1Δ | MATa his3 leu2 met15 ura3 upf1:KanMX6 | (Baker and Parker 2006) |

TABLE 1-continued

Genotypes of strains used in this study.

| Strain | Genotype | Source |
|---|---|---|
| TD76-8D | MATa his4-303(ATT) ura3-52 leu2-3 | Thomas Donahue |
| 301-4D | MATa leu2-3 leu2-112 ura3-52 his4-303(ATT) sui1-1 | (Yoon and Donahue 1992) |
| 117-1AR7 | MATa his4-303(ATT) ura3-52 ino1-13 sui3-2 | (Donahue et al. 1988) |
| H1894 | MATa ura3-52 leu2-3 leu2-112 trp1-Δ63 gcn2Δ | (Kawagishi-Kobayashi et al. 1997) |
| H3984 (JCY149) | MATa ura3-52 leu2-3 trp1Δ63 his4-303(ATT) sui1-Δ'::hisG [p4389 His-SUI1 LEU2 2 micron] | (Cheung et al. 2007) |
| BY4743 | MATa/αhis3Δ37/his3Δ1 leu2Δ0/leu2Δ0 LYS2/lys2Δ0 met15Δ0/MET15 ura3Δ0/ura3Δ0 | Open Biosystems |
| YNL244C (+/sui1Δ) | MATa/αhis3Δ37/his3Δ1 leu2Δ0/leu2Δ0 LYS2/lys2Δ0 met15Δ0/MET15 ura3Δ0/ura3Δ0 +/sui1Δ | Open Biosystems |
| YMR260C (+/tif11Δ) | MATa/αhis3Δ38/his3Δ1 leu2Δ0/leu2Δ0 LYS2/lys2Δ0 met15Δ0/MET15 ura3Δ0/ura3Δ0 +/tif11Δ | Open Biosystems |
| YPR041W (+/tif5Δ) | MATa/αhis3Δ38/his3Δ1 leu2Δ0/leu2Δ0 LYS2/lys2Δ0 met15Δ0/MET15 ura3Δ0/ura3Δ0 +/tif5Δ | Open Biosystems |
| JCY145 | MATa ura3-52 leu2-3 leu2-112 trp1Δ63 his4-303(AUU) sui1Δ::hisG pCFB03 (sc LEU2 His-SUI1) | (Cheung et al. 2007) |
| JCY653 | MATa ura3-52 leu2-3 leu2-112 trp1Δ63 his4-303(AUU) sui1Δ::hisG pCFB03 (sc LEU2 His-SUI1-G107S) | (Nanda et al. 2009) |
| JCY189 | MATa ura3-52 leu2-3 leu2-112 trp1Δ63 his4-303(AUU) sui1Δ::hisG pCFB129 (sc LEU2 His-SUI1-ISQLG93-97ASQAA) | (Cheung et al. 2007) |
| H3582 | MATa ura3-52 trp1Δ63 leu2-3 leu2-112 his4-301 (ACG) tif11Δp3392 (sc TIF11, URA3) | (Fekete et al. 2005) |
| ASY36 | MATa ura3-52 trp1Δ63 leu2-3 leu2-112 his4-301 (ACG) tif11ΔpAS36 (hc tif11-Δ107-153, URA3) | (Saini et al.) |
| ASY113 | MATa ura3-52 trp1Δ63 leu2-3 leu2-112 his4-301 (ACG) tif11ΔpAS113 (hc tif11-Δ124-153, URA3) | This study |

To construct the uORF-luciferase fusion reporters, the PRE2 uORF was fused to the firefly luciferase coding region with a PDR5 3'UTR as NotI/SpeI fragments in pRS313. The (Spe1)-Fluc-3'UTR fusion was cloned by PCR with oNTI226 (GCAactagtGGAAGACGCCAAAAACATAAAG (SEQ ID NO: 1)) and oNTI227 (GCTttaattaaTTACACGGC-GATCTTTCCG (SEQ ID NO: 2)) on pGL3basic and PCR with oNTI228 (GCAttaatTAATAGAATTTTGAATTTG-GTTAAGAAAAG (SEQ ID NO: 3)) and oNTI229 (GCTgggcccATCAGAGCTGGTAAATTCAAG (SEQ ID NO: 4)) from yeast genomic DNA. A 3-way Spe1/Pac1/Apa1 ligation fused Fluc with the PDR5 3'UTR in the pRS313 background. The in-frame PRE2 uORF plasmid (pNTI33) was made by PCR with primer oNTI248 (GCAactagtTCTAT-TCAATTTAATAGTAAATTTGTTATT (SEQ ID NO: 5)), and the out-of-frame plasmid (pNTI32) was made using the primer oNTI249 (GCAactagtATCTATTCAATTTAATAG-TAAATTTGTTAT (SEQ ID NO: 6)), in combination with oNTI247 (GCTgcggccgcGTTACTATCAAGATG-TATCAAACAATG (SEQ ID NO: 7)), and subcloned into the Fluc-PDR5 3'UTR plasmid as a Not1/Spe1 fragment.

TIF11 mutant alleles were constructed by fusion PCR using p3390, containing WT TIF11 as template, as described previously (Olsen et al. 2003). The fusion PCR products were inserted between the EcoRI and SalI sites of YCplac111 (sc) or YCplac181 (hc), and the subcloned fragments of all mutant constructs were confirmed by DNA sequencing. Yeast strains harboring the mutant constructs were constructed from strains H3582 (his4-301) (Fekete et al. 2005) by plasmid shuffling.

Chemicals

After initial characterization of NSC218351 from the NCI DTP library, additional material was purchased from Sigma Aldrich for further studies. It behaved identically to the compound in the library. NSC92218 could not be obtained commercially and thus came only from the NCI DTP. Identity and purity of NSC92218 were confirmed by mass spectrometry at the University of Illinois at Urbana Champaign facility. One species with an exact ionized mass of 287.1 was detected by LR ESI, and HR Q-tof gave the possible atomic composition of $C_9H_8N_2O_1$ or $C_7H_9N_2ONaI$. The expected atomic mass, 286.1, and composition $C_9H_8N_2OI$ exactly matched NSC92218. Cycloheximide was obtained from Sigma Aldrich.

Example 1

Screening Protocols

In this study, a high throughput screen in *S. cerevisiae* was set up using a dual luciferase reporter to find compounds that alter the fidelity of start codon selection in vivo. Approximately 55,000 compounds were screened, and structurally related molecules were identified that increase the use of non-AUG codons as initiation sites, thus chemically inducing Sui⁻ phenotypes. Data indicate that these compounds act within the cell and that they increase initiation at a natural uORF with a near-cognate start codon as well as on the luciferase reporter mRNA. The compounds can also increase growth on medium lacking histidine of a Sui⁻ strain of yeast (sui1-1) in which the AUG start codon of the HIS4 gene has been changed to a near-cognate codon such that initiation must occur at a non-AUG (his4-303). This effect demonstrates the feasibility of chemically ameliorating a genetic defect caused by mutation of an initiation codon.

Figure 2:
FIG. 2 is an overview of the dual luciferase assay and screen.

A dual luciferase assay was previously used to measure the efficiency of translation in yeast and was used to measure translation from near-cognate start codons in wild type and Sui⁻ mutant yeast strains that exhibit defects in fidelity of start site selection (Cheung et al., Genes Dev., vol. 21, no. 10, pp. 1217-1230, 2007; Kolitz et al., RNA, vol. 15, no. 1, pp. 138-152, 2009). In the assay, Renilla luciferase (Rluc) and firefly luciferase (Fluc) genes are expressed from a single plasmid, each under the control of a separate constitutive promoter and terminator, allowing transcription of the two genes as separate mRNAs. The Fluc mRNA has a non-AUG start codon (FIG. 2A). The Rluc mRNA has an AUG start codon and acts as an internal control for effects on global gene expression and cell growth (as well as pipetting errors or differences in lysis efficiency), enabling detection of effects specific to initiation on the Fluc mRNA. In both WT and Sui⁻ strains, Fluc activity is detectable when the AUG start codon is changed to near-cognate codons that differ from AUG by only one base (UUG, GUG, CUG, AUA, AUC, AUU, ACG), except AAG and AGG. UUG is used ~5% as well as AUG in wild type yeast (Kolitz et al., RNA, vol. 15, no. 1, pp. 138-152, 2009), and almost as well as AUG in some Sui⁻ strains (Cheung et al., Genes Dev., vol. 21, no. 10, pp. 1217-1230, 2007). UUG was chosen as the near cognate start site in the screen, allowing easy identification of compounds that either increase expression (chemically reproducing a Sui⁻ phenotype, decreasing fidelity) or decrease expression (enhancing fidelity) of UUG relative to AUG in the dual luciferase assay.

The scheme for identifying compounds that altered the fidelity of translation initiation is shown in FIG. 2B. If a compound appeared to be toxic in the primary screen (both luciferase values near background levels), it was screened again at lower concentrations. Compounds that altered the UUG/AUG ratio by greater than 1.5-fold were rescreened. If the UUG/AUG ratio change was reproducible, the compounds were counter-screened using the dual luciferase assay in which both reporters had AUG start codons. The counter-screen is very powerful, eliminating any compounds that have effects unrelated to the fidelity of start codon recognition. For example, a compound that alters the activity of one of the luciferase enzymes or that generally affects translation of the Fluc mRNA will show an effect in the counter-screen assay as well as the primary screen, whereas compounds that specifically affect initiation from non-AUG codons will not. Compounds that produced similar effects in both the initial screen and the counter-screen (for example, increased both UUG/AUG and AUG/AUG) were not pursued further. For the few compounds that passed the counter-screen, the luciferase ratios, both UUG/AUG and AUG/AUG, were measured at various concentrations of each drug to demonstrate concentration dependence. The compounds were then tested in secondary assays.

Dual Luciferase Assay

The dual luciferase assay was carried out as in Kolitz et al. (RNA, vol. 15, no. 1, pp. 138-152, 2009), with the following modifications to screening conditions: An over-night culture of wild type yeast (BY4741 transformed with pFuugRaug) were diluted to an $OD_{600}$ of approximately 0.2 in SC-Ura, and 50 µL were aliquoted to each well of a 96 well plate. BY4741 expressing the RaugFaug plasmid was included in the 1ˢᵗ and last column as an additional control. Compounds to be tested were supplied from the NCI DTP library in 96 well format at 1 mM in DMSO. DMSO was included in all control wells. 1.5 µL of compound (or DMSO) was added to each well of the yeast plate, followed by incubation at 30° C. for 4 hours while shaking. To measure luciferase activity, 1 µL of culture was added directly to 50 µL of 1× Passive Lysis Buffer (Promega), incubated 40-60 minutes at room temperature, then luciferase activity measured using a Turner Modulus Microplate Reader (Kolitz et al., RNA, vol. 15, no. 1, pp. 138-152, 2009). The same protocol was used when testing the other libraries, with the appropriate solvent controls. The Fuug/Raug ratio of each sample with drug was compared to the average Fuug/Raug ratio of the solvent only controls on the same plate.

Every row contains DMSO-only controls for each strain. For each compound-treated sample, the ratio of [Fluc(UUG)/Rluc(AUG)]/[Fluc(AUG)/Rluc(AUG)] is calculated using the DMSO-only Fluc(AUG)/Rluc(AUG) control from that row (there is one for each row in a plate). This ratio is the Fluc(UUG)/Fluc(AUG) ratio normalized to Rluc(AUG) activity in each sample. This normalization helps to control for any overall change in the observation of active luciferase enzymes that is not caused by addition of drug between the drug-containing (Fluc(UUG)) and DMSO-only (Fluc(AUG)) wells. Potential changes include pipetting inaccuracies, differences in lysis efficiencies or global effects on gene expression due to differences in cell densities during growth. The internal Rluc control also helps screen out compounds that affect gene expression or cell growth globally rather than having specific effects on translation from non-AUG codons.

Screening Assay Validation and Controls

Figure 3:
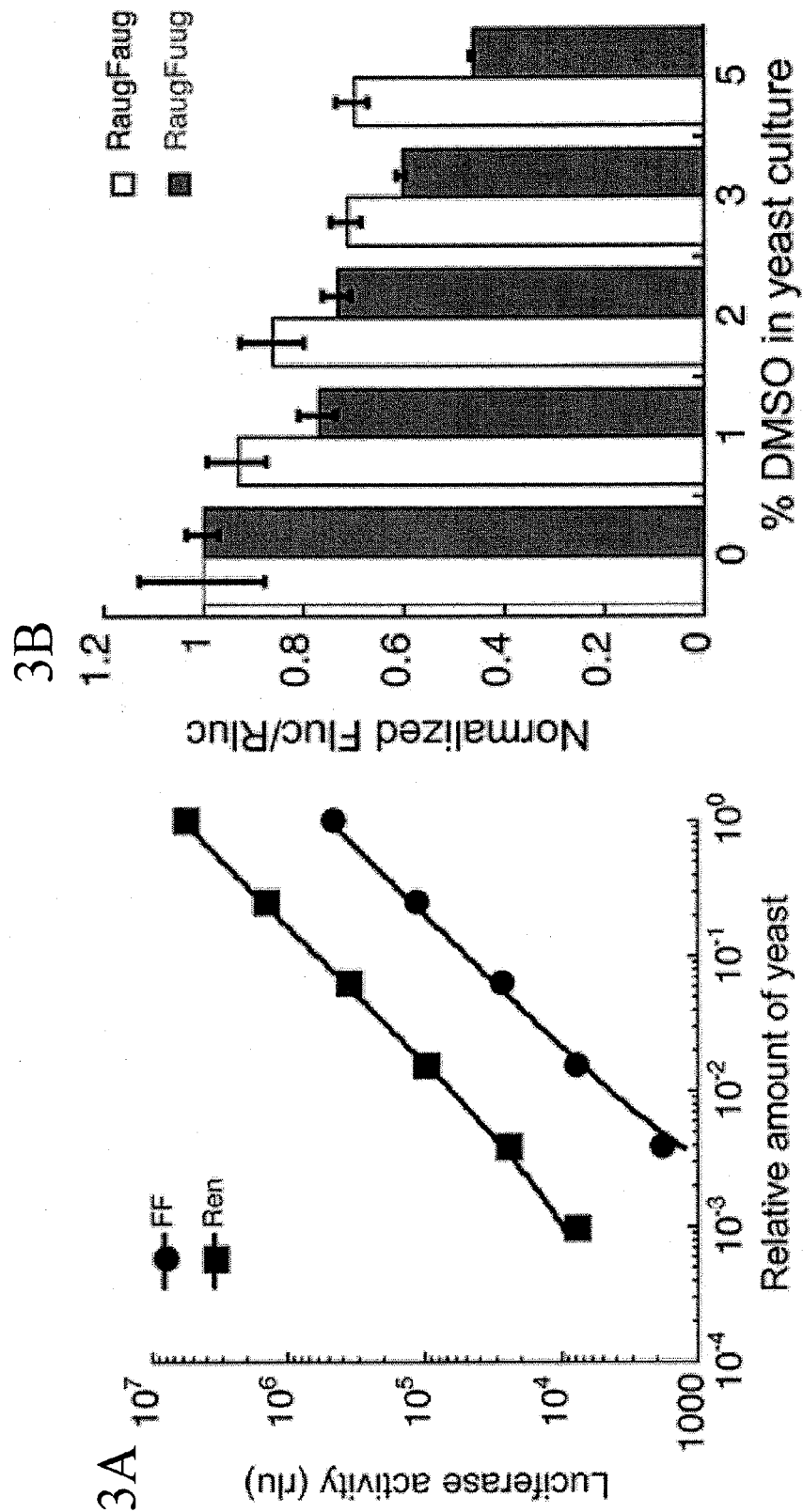
FIG. 3 shows an evaluation of the dual luciferase assay under screening conditions.
Figure 4:
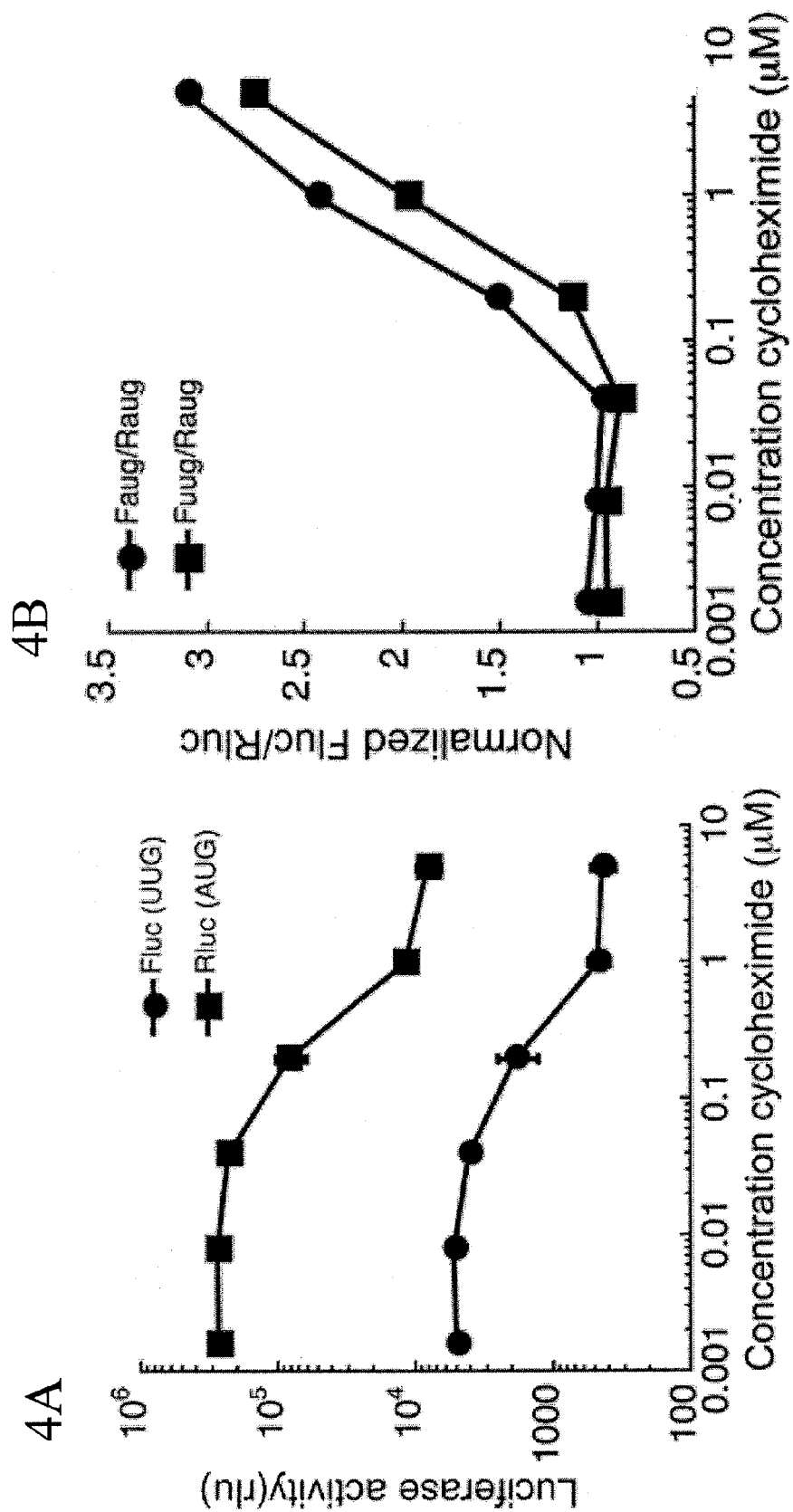
FIG. 4 shows an evaluation of the dual luciferase assay under screening conditions.

To demonstrate that the dual luciferase assay could be adapted to a high throughput screen, the activities of each reporter were characterized and the ratio of Fluc to Rluc calculated under screening conditions. For screening, yeast were grown in 96 well plates, then added to Passive Lysis Buffer (Promega) in a luciferase reading plate, and the activity of both reporters measured. Luciferase detection is linear over at least 3-orders of magnitude (FIG. 3A), indicating that an increase or decrease in expression of either reporter should be detectable. When the cells were grown under screening conditions in the presence of cycloheximide, an inhibitor of translation elongation, the raw luciferase values dropped to ~25% of the control values (FIG. 4A); cycloheximide also caused a change in both ratios, $Fluc_{UUG}/Rluc_{AUG}$ and $Fluc_{AUG}/Rluc_{AUG}$ (FIG. 4B), possibly because of differences in half-lives of the two proteins. The Fluc protein has a half life of 1.5 hrs in yeast, but the half life of Rluc has not been measured (McNabb et al., Eukaryot. Cell, vol. 4, no. 9, pp. 1539-1549, 2005). Since cycloheximide altered the $Fluc_{UUG}/Rluc_{AUG}$ ratio, general translation inhibitors can be identified in the primary screen. However, such compounds will fail the counter screen because the $Fluc_{AUG}/Rluc_{AUG}$ ratio is also altered (FIG. 4B, circles).

The compounds were dissolved in DMSO. Addition of DMSO alone to growth media resulted in a slight change in the $Fluc_{UUG}/Rluc_{AUG}$ ratio (FIG. 3B). DMSO controls were included in the screen and were used to correct for the effect of DMSO on the $Fluc_{UUG}/Rluc_{AUG}$ and $Fluc_{AUG}/Rluc_{AUG}$ ratios.

Figure 5:
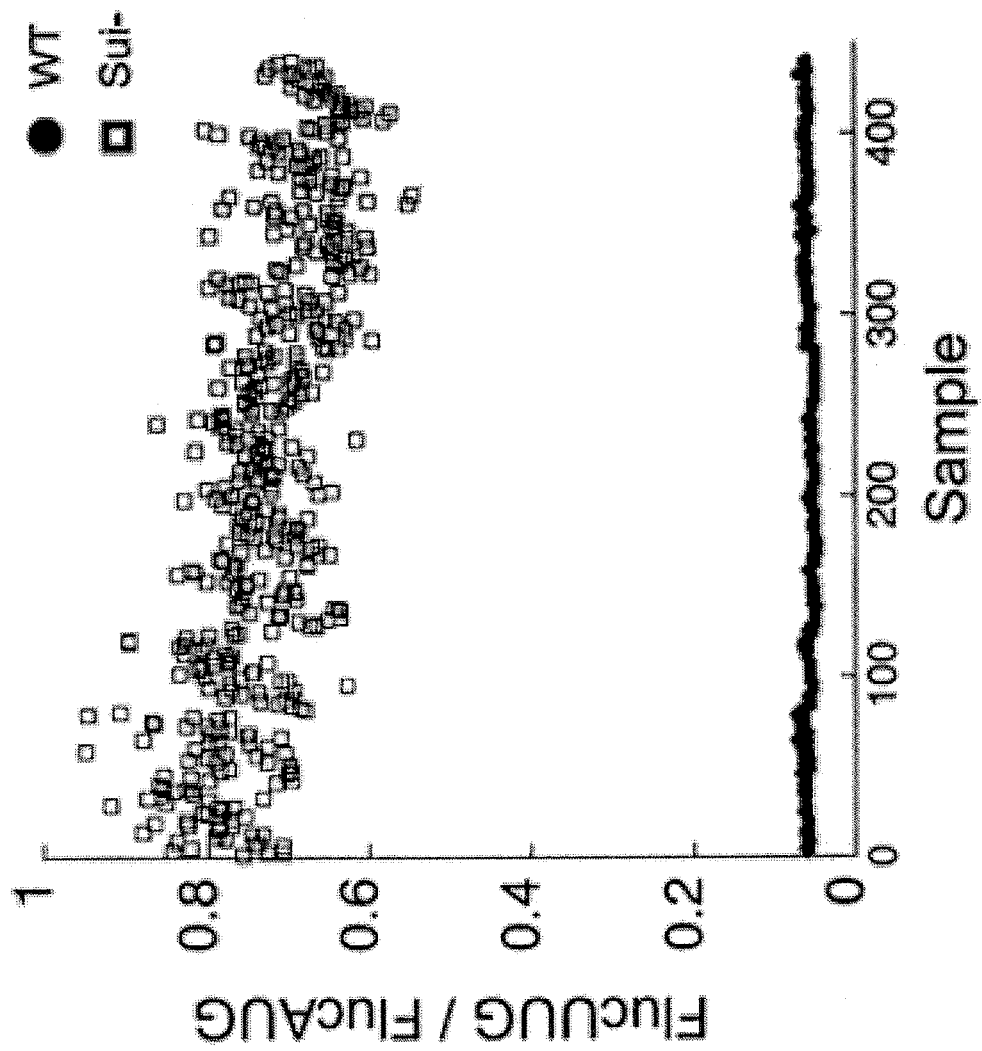
FIG. 5 shows the data set used to calculate the Z' factor. The FlucUUG/FlucAUG ratios were measured using a wild type (TD76-8D, closed circles) and a Sui⁻ strain (301-4D, open squares).

Unfortunately, no compound that alters the fidelity of start codon recognition is currently known, and thus a positive control was not available to include in the screen. However, the Sui⁻ mutant strains, which decrease the fidelity of start codon recognition by up to 20-fold, can serve as proxy positive controls to evaluate the quality of the assay. The UUG/AUG ratio of the sui1-1 mutant (eIF1 D83G, which increases translation from UUG almost to the level of AUG) (Cheung et al., Genes Dev., vol. 21, no. 10, pp. 1217-1230, 2007;

Donahue et al., *Mol. Cell. Biol.*, vol. 8, no. 7, pp. 2955-2963, 1988) compared to the UUG/AUG wild type ratio gives a Z'-factor of 0.68 (FIG. 5). The Z'-factor was calculated using the formula $Z'=1-(3\sigma_{c+}+3\sigma_{c-})/(|\mu_{c+}-\mu_{c-}|)$ where c+ is the FlucUUG/AUG ratio from the sui1-1 strain (301-4D) and c− is the same ratio from the wild type strain (TD76-8D). σ represents standard deviation, and μ represents average (Zhang et al., *J. Biomol. Screen.*, vol. 4, no. 2, pp. 67-73, 1999). The Z' factor is a statistical characterization to evaluate the quality of a screening assay. According to these parameters, the dual luciferase assay is well suited to identify compounds that change the fidelity of translation initiation.

Counterscreening

Changes in the Fluc(UUG)/Rluc(AUG) ratio could be caused by a compound altering the use of UUG as a start codon (the desired target) or a variety of other effects such as changes in transcription of one gene, changes in mRNA or protein half-life, or inhibition or activation of one of the luciferase enzymes. To eliminate compounds that do not target the fidelity of start codon recognition, we use the same dual luciferase assay but with a plasmid in which both firefly and *renilla* luciferase mRNAs have AUG start codons. Compounds that specifically increase use of near-cognate codons as start sites will not produce an effect in this Fluc(AUG)/Rluc(AUG) assay, whereas compounds that alter other process will not be specific for the Fluc(UUG)/Rluc(AUG) system and will still produce effects with the Fluc(AUG)/Rluc(AUG) reporter. Compounds that are not specific for effects on Fluc(UUG) expression will not be pursued further. This counter-screen is extremely powerful and eliminated 99.8% of the initial hits (1,000) from the 50,000 molecules we screened from the DTP library.

Pre-Lysis Experiments

Additionally, a "prelysis" experiment, where the compound is added to yeast lysates, eliminates compounds that specifically inhibit the luciferase enzymes. Yeast were grown for four hours with compound or DMSO. The ratio of firefly luciferase with compound was compared to that with DMSO only, each firefly value was normalized to internal RlucAUG control. A decrease in the ratio indicates increased expression of firefly luciferase. In prelysis samples, the yeast were grown without compound, and compound was added to the lysate before measuring luciferase activity to control for inhibition of luciferase enzymes.

Hit Validation

Concentration Dependence

When a hit was identified, rescreening and counter screening assays were done using 300 μM to 10 nM of the compound, i.e., the identified "hit," to measure concentration dependence.

uORF Luciferase Assay

BY4741 was transformed with pNTI33 or pNTI32. Transformants were incubated with compound and luciferase activity measured as described for the dual luciferase assay. The solvent-only firefly luciferase activity was used for normalization.

To further validate the effects of compounds that pass the primary and counterscreens, an additional reporter assay was performed. The assay uses a 5'-upstream open reading frame (uORF) that begins with a UUG codon and was shown in yeast to be translated, especially under amino acid starvation conditions (Castilho-Valavicius et al., Genetics, vol. 124, pp. 483-495, 1990). This uORF was fused both in-frame and out-of-frame to the firefly luciferase gene and the effect of the compounds on initiation on this physiologically relevant near-cognate start codon assessed. Active compounds increase expression of the in-frame fusion, but not the out-of-frame fusion, to a similar or greater extent than they do with the original luciferase reporter with a UUG start codon. This indicates the compounds can enhance use of UUG codons in multiple sequence contexts.

RT-q-PCR

With both luciferase-based reporters, RT-q-PCR was used to provide further evidence that the compounds do not affect mRNA abundance. The effect of the compounds with these reporters was tested in strains in which nonsense-mediated decay is inoperative (upf1Δ) to further confirm that mRNA stability is not altered.

Growth Assays

An additional reporter assay utilizes a yeast strain in which the AUG start codon of the HIS4 gene has been changed to AUU (his4-303) (Huang et al., Genes Dev., vol. 11, pp. 2396-2413, 1997). This strain is a histidine auxotroph and cannot grow on medium lacking histidine. However, Sui⁻ mutations allow initiation from the AUU start site or, more commonly, a UUG three codons downstream from it, restoring expression of His4p and thus growth on His⁻ medium (Castilho-Valavicius et al., Genetics, vol. 124, pp. 483-495, 1990; Huang et al., Genes Dev., vol. 11, pp. 2396-2413, 1997; Yoon et al., Mol. Cell. Biol., vol. 12, pp. 248-260, 1992). Observing an alteration of the Sui⁻ phenotype is a more sensitive assay than rescuing growth of a wild type strain. If a compound enhances translation from UUG, growth of these mutants should be better with compound than without on His⁻ media. Likewise, if the compound increases the fidelity of initiation, then growth should be compromised.

Yeast with the his4-303 allele from an over-night culture were washed with water and diluted to an $OD_{600}$ between 0.1-1. Strips of sterile Whatman paper were soaked with compound or solvent and placed on an agar plate of the appropriate media. The yeast culture was spotted onto the plate at various distances from the paper strips. The plates were incubated at 30° C. Diffusion creates a gradient of compound, which tends to enhance growth only in a certain range because of off-setting toxicity at high concentrations.

In Vitro Transcription Assays

An in vitro translation system was also used. This assay uses yeast extracts to translate in vitro transcribed mRNAs encoding *renilla* luciferase with an AUG or UUG start codon (Wu et al., Methods Enzymol., vol. 429, pp. 203-225, 2007).

Example 2

Active Compounds

Approximately 55,000 compounds from four libraries were screened. The main source of compounds was the National Cancer Institute (NCI) Developmental Therapeutics Program (DTP) library. Of the >200,000 compounds in this library, 49,840 were screened. Three smaller libraries were also screened: 1) ~2500 compounds that have passed phase I clinical trials (gift of Dr. Jun Liu, Johns Hopkins University School of Medicine); 2) ~2500 natural products (Dr. Jerry Pelletier); 3) ~500 microbial growth media extracts (gift of Dr. Scott Strobel, Yale University). With the liberal cut-off of a ≥1.5-fold change in the $Fluc_{UUG}/Rluc_{AUG}$ ratio, approximately 2% of the compounds screened passed the primary screen, but 2 compounds, both from the NCI DTP library, passed the counter-screen. The structures of these two compounds, isoquinoline-1-carboxylic acid (NSC218351) and 7-amino-5-iodo-8-quinolinol hydrochloride (NSC92218), are shown below. NSC218351 is commercially available through Sigma Aldrich. NSC92218 is not commercially available, and was supplied by the NCI for further studies.

High resolution mass spectrometry confirmed the purity and atomic composition of this compound.

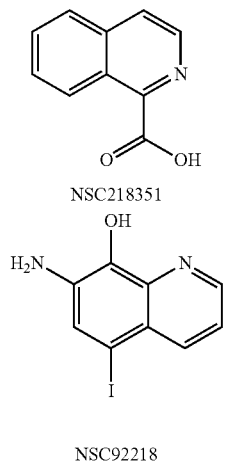

NSC218351

NSC92218

Pre-Lysis Experiments

Figure 6:
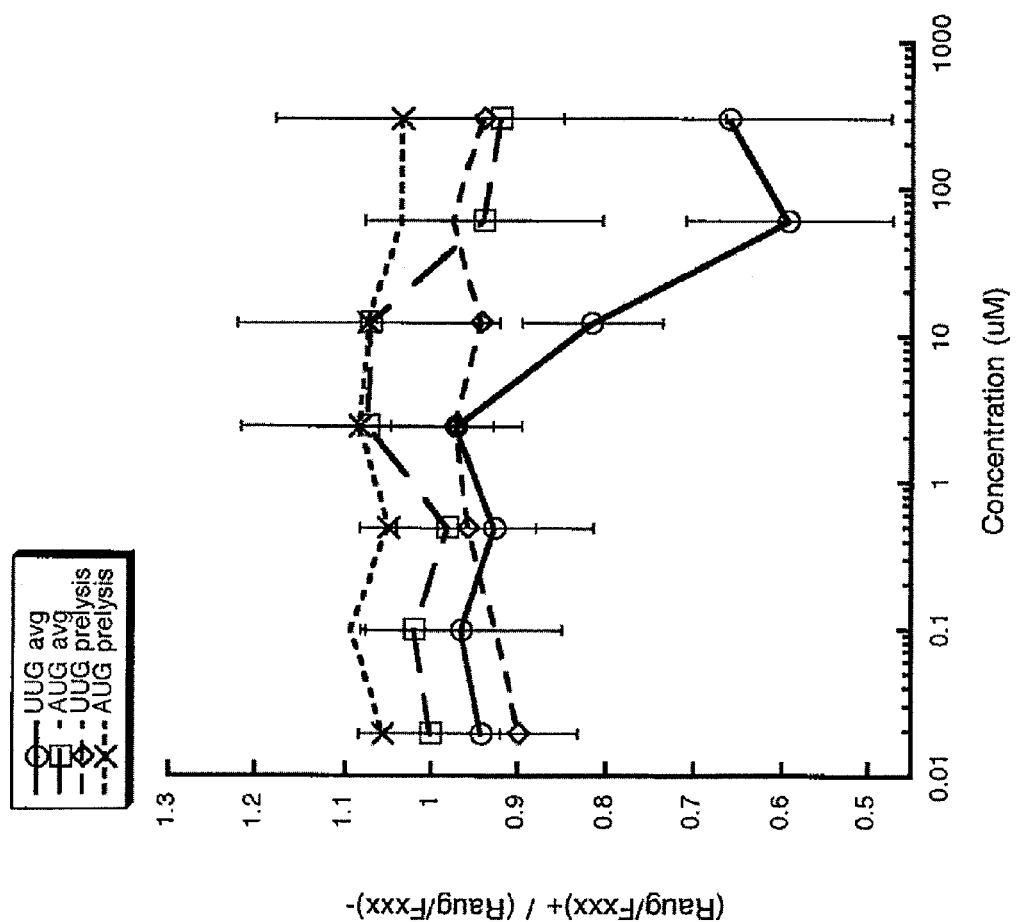
FIG. 6 shows the effect of compound NSC 218351 on expression of firefly luciferase in a pre-lysis experiment. Points are averages of twelve independent experiments for in vivo ratios, and prelysis points are from one experiment.

FIG. 6 demonstrates the effect of compound NSC 218351 on expression of firefly luciferase in the pre-lysis experiment. Points are averages of twelve independent experiments for in vivo ratios, and prelysis points are from one experiment;

Concentration Dependence

Figure 7:
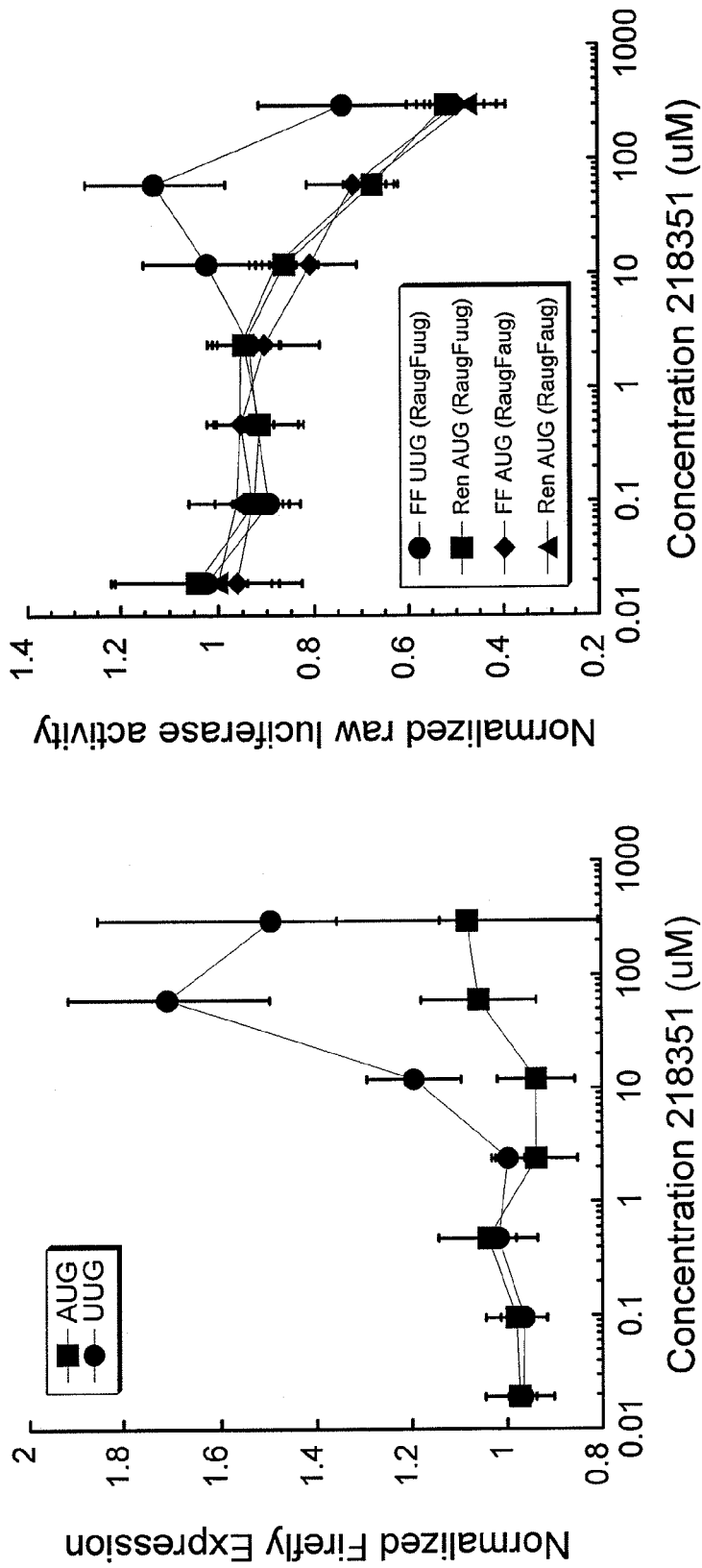
FIG. 7 shows the effects of NSC218351 in the dual luciferase assay.

NSC218351 increased the $Fluc_{UUG}/Rluc_{AUG}$ ratio 1.8-fold (FIG. 7A). The raw $Fluc_{UUG}$ value increased slightly as the $Rluc_{AUG}$ value decreased (FIG. 7B). At high concentrations all values decreased, suggesting a general effect on translation and/or toxicity. The $Fluc_{AUG}/Rluc_{AUG}$ ratio does not change in the presence of compound (FIG. 7A, squares), even when both raw values decreased at high concentrations of compound (FIG. 7B).

Figure 8:
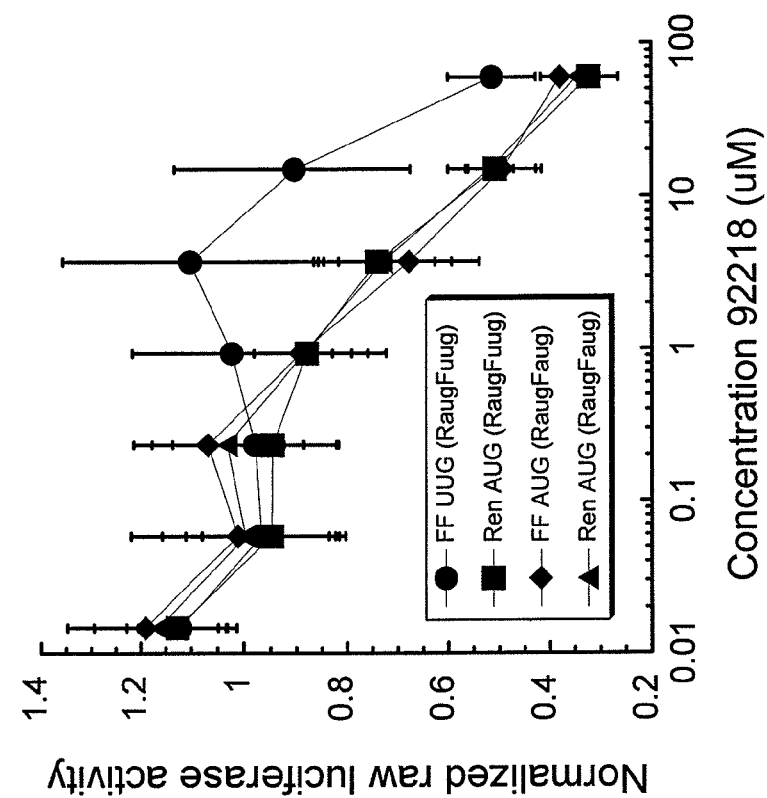
FIG. 8 shows the effects of NSC92218 in the dual luciferase assay.
Figure 8:
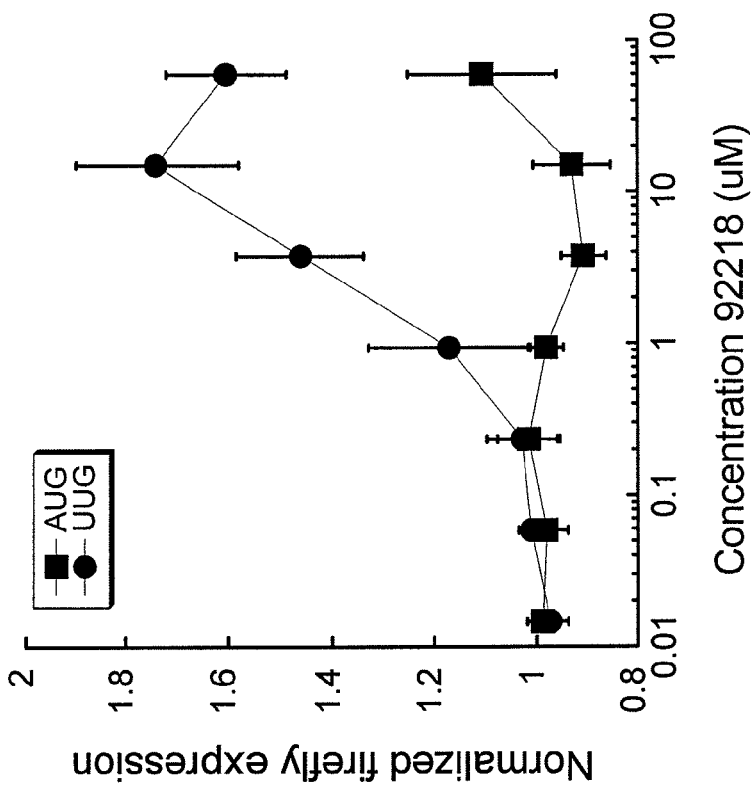

NSC92218 affected the dual luciferase assay in a similar manner to NSC218351. The $Fluc_{UUG}/Rluc_{AUG}$ ratio increased 1.8-fold, while the $Fluc_{AUG}/Rluc_{AUG}$ ratio did not change (FIG. 8A, compare circles to squares). The raw FlucUUG value did not change, or increases slightly, at concentrations that decreased the other luciferase values (FIG. 8B).

Figure 9:
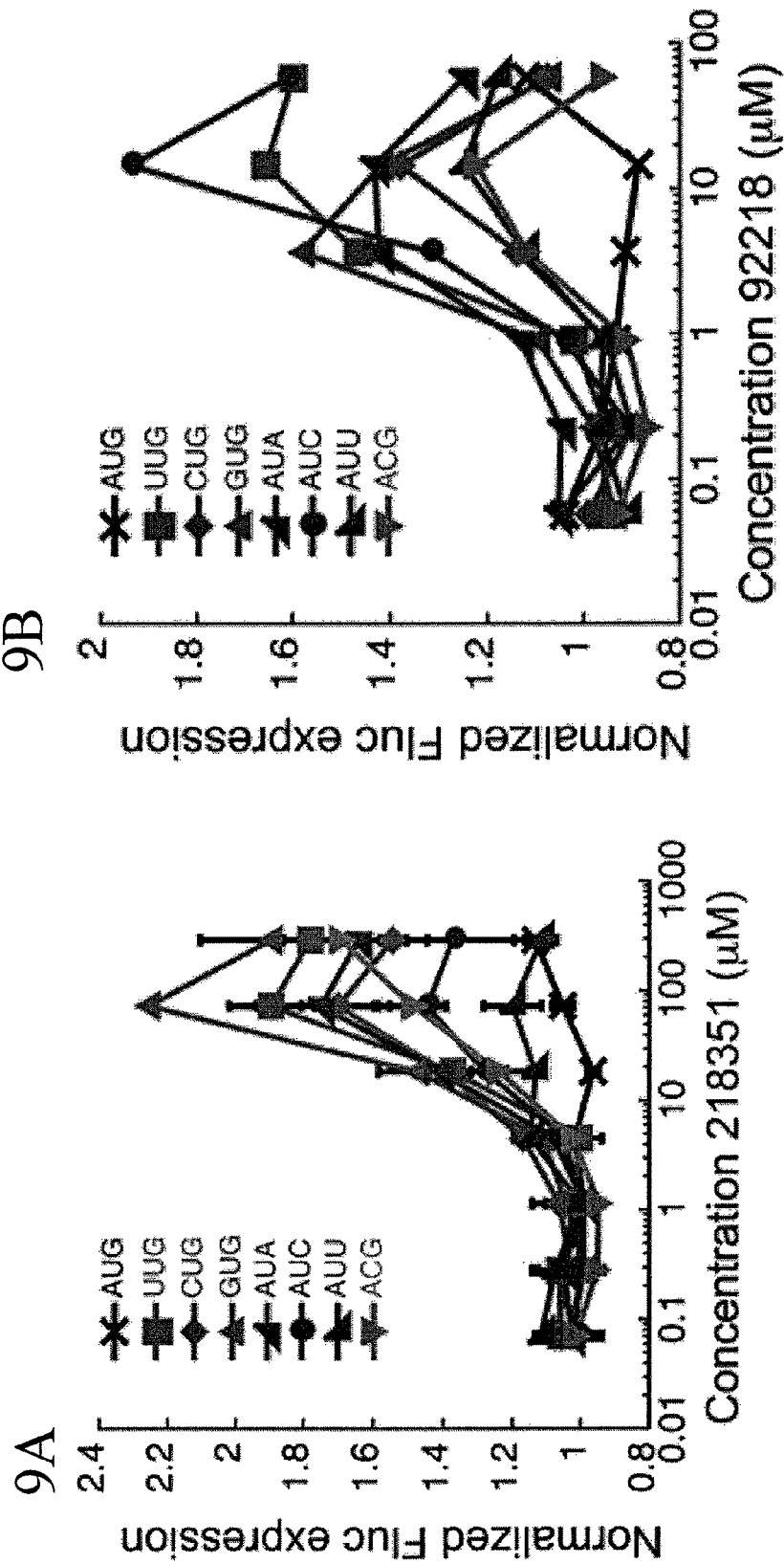
FIG. 9 shows Fluc expression from different near-cognate start codons.

The compounds increased initiation at most near-cognate codons, indicating that their effects are not limited to UUG codons (FIGS. 9A and 9B). AAG and AGG are not used detectably as Fluc initiation codons in yeast (Kolitz et al., RNA, vol. 15, no. 1, pp. 138-152, 2009) and were thus not tested. The one exception is that NSC218351 did not increase initiation at AUU codons. Interestingly, AUU is generally the near cognate codon whose use as an alternative start site is increased the least by Sui⁻ mutants (FIG. 10). Efficiency of use of near cognate codons as initiation sites was measured with the dual luciferase assay in several Sui⁻ mutant strains. Translation from each alternative start codon in the Sui⁻ strain was normalized to translation from that codon in a wild type strain. Sui⁻ mutations increase the use of near cognates up to 18-fold (GUG in eIF1 D83G strain). However, in each mutant strain, translation from AUU is increased the least. Although it is not understood why AUU behaves anomalously, it is interesting that NSC218351 mimics this aspect of the behavior of the Sui⁻ mutations in initiation factors.

RT-PCR

RNA was purified from yeast (grown with 50 µM NSC218351 or 2 µM NSC92218) using acid phenol extraction (Fazzio et al., Mol. Cell. Biol., vol. 21, no. 19, pp. 6450-6460, 2001), and DNase treated (DNase I, Roche). The iScript cDNA kit (BioRad) was used to make the cDNA, and the SYBR green protocol was used for the qPCR reactions in a BioRad CFX96 Real-time PCR detection system.

Figure 11:
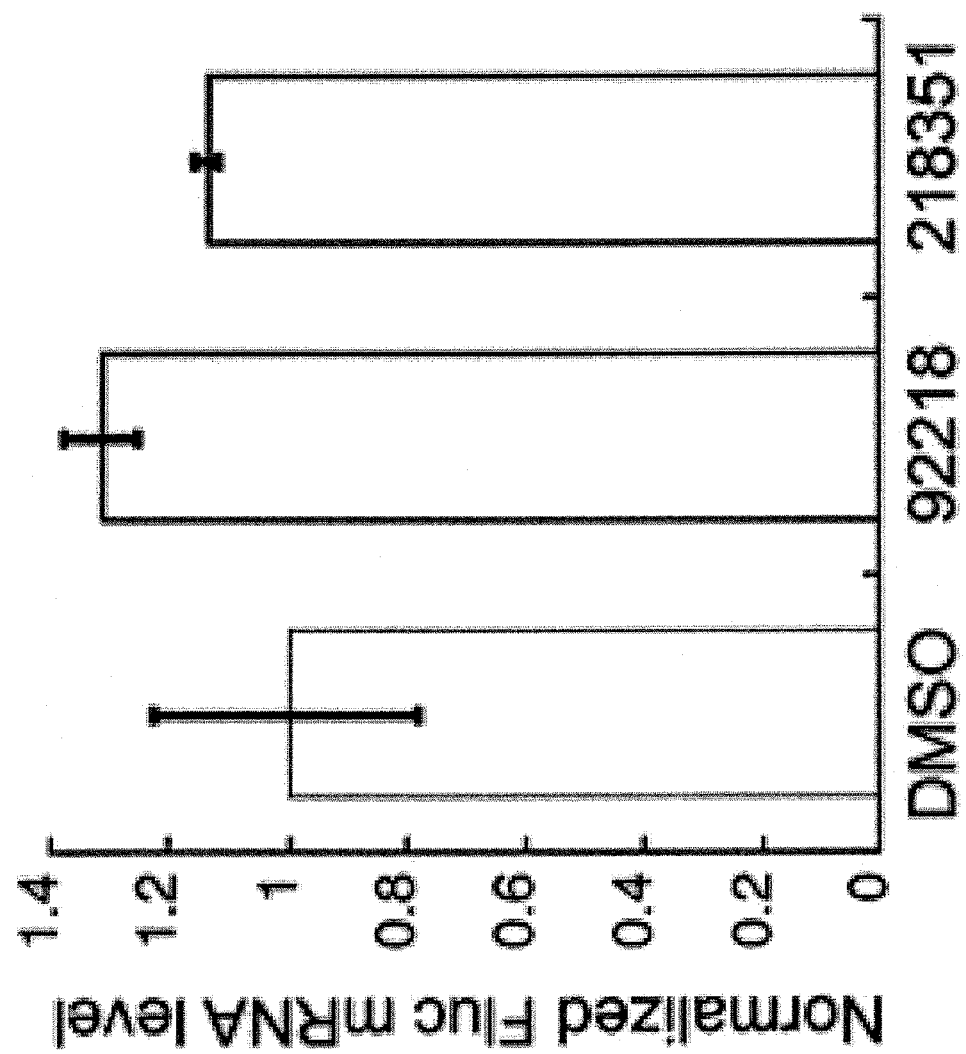
FIG. 11 shows relative levels of Fluc/Rluc mRNA measured using RT-q-PCR, from strain BY4741 expressing FlucUUG and RlucAUG treated with 2 μM NSC92218 or 50 μM NSC218351. The Rluc mRNA levels were used to normalize the Fluc mRNA levels, and the Fluc/Rluc ratio of the DMSO sample was used to normalize the samples treated with compounds. Data are the averages of duplicate samples.

At high concentrations, the compounds slow yeast growth; however, the $Fluc_{UUG}/Rluc_{AUG}$ ratio increases at concentrations of compounds that do not affect growth of wild type yeast (50 µM NSC218351 and 2 µM NSC92218, FIGS. 8A and 9A). To demonstrate that the compounds were not affecting mRNA levels at these concentrations, RT-q-PCR (reverse-transcription, quantitative PCR) was used to measure relative levels of the luciferase mRNAs. The levels of the reporter messages did not change significantly (FIG. 11), indicating that the compounds do not affect synthesis or degradation of these mRNAs.

Non-Sense Mediated Decay

As an additional test for effects on mRNA stability, the compounds in the dual luciferase assay were tested with a strain deficient for non-sense mediated decay (NMD), upf1Δ (He et al., Mol. Cell. Biol., vol. 23, no. 15, pp. 5431-5445, 1993). Premature termination can target a message for NMD. If a message lacks the appropriate start codon, use of an upstream or out of frame codon for initiation can lead to premature termination, and potentially NMD (Amrani et al., Nat. Rev. Mol. Cell. Biol., vol. 7, no. 6, pp. 415-425, 2006. Expression from the UUG codon in Fluc mRNA was not changed in the upf1Δ strain relative to the WT strain (in the absence of compound), indicating that NMD does not influence expression of this reporter when it lacks an AUG start codon (Kolitz et al., RNA, vol. 15, no. 1, pp. 138-152, 2009). If the compounds were inhibiting the NMD pathway, no effect would be expected in the assay in a strain where NMD was already blocked. Using the dual luciferase assay, the effects of the compounds on the UUG/AUG ratio were still observed in the upf1Δ strain (data not shown).

These results, in combination with the RT-q-PCR experiments and the fact that no effect is seen on the $Fluc_{AUG}/Rluc_{AUG}$ expression ratio, indicate that the compounds increase expression of the reporter from non-AUG start codons at the translational level.

Time Dependence

Based on the measured activities of Sui⁻ mutants (Cheung et al., Genes Dev., vol. 21, no. 10, pp. 1217-1230, 2007) (FIG. 10), yeast cells are viable even when translation from near cognate start codons is increased almost 20-fold relative to WT cells. To investigate if ~2 fold is the maximal effect of the compounds on expression from the Fluc reporter a determination of whether time of incubation with compound altered the UUG/AUG expression ratio was conducted. Under screening conditions, yeast was grown with compounds for 4 hours. The UUG/AUG and AUG/AUG ratios from 1 to 8 hours of growth with compound were monitored. At 1 hour, no effect of either compound was observed. Approximately 20% of the maximal effect was achieved at 2 hours. The maximal effect is reached at 4 hours, and further incubation did not result in an additional decrease in the fidelity of start site selection (data not shown).

Other Yeast Strains

Figure 12:
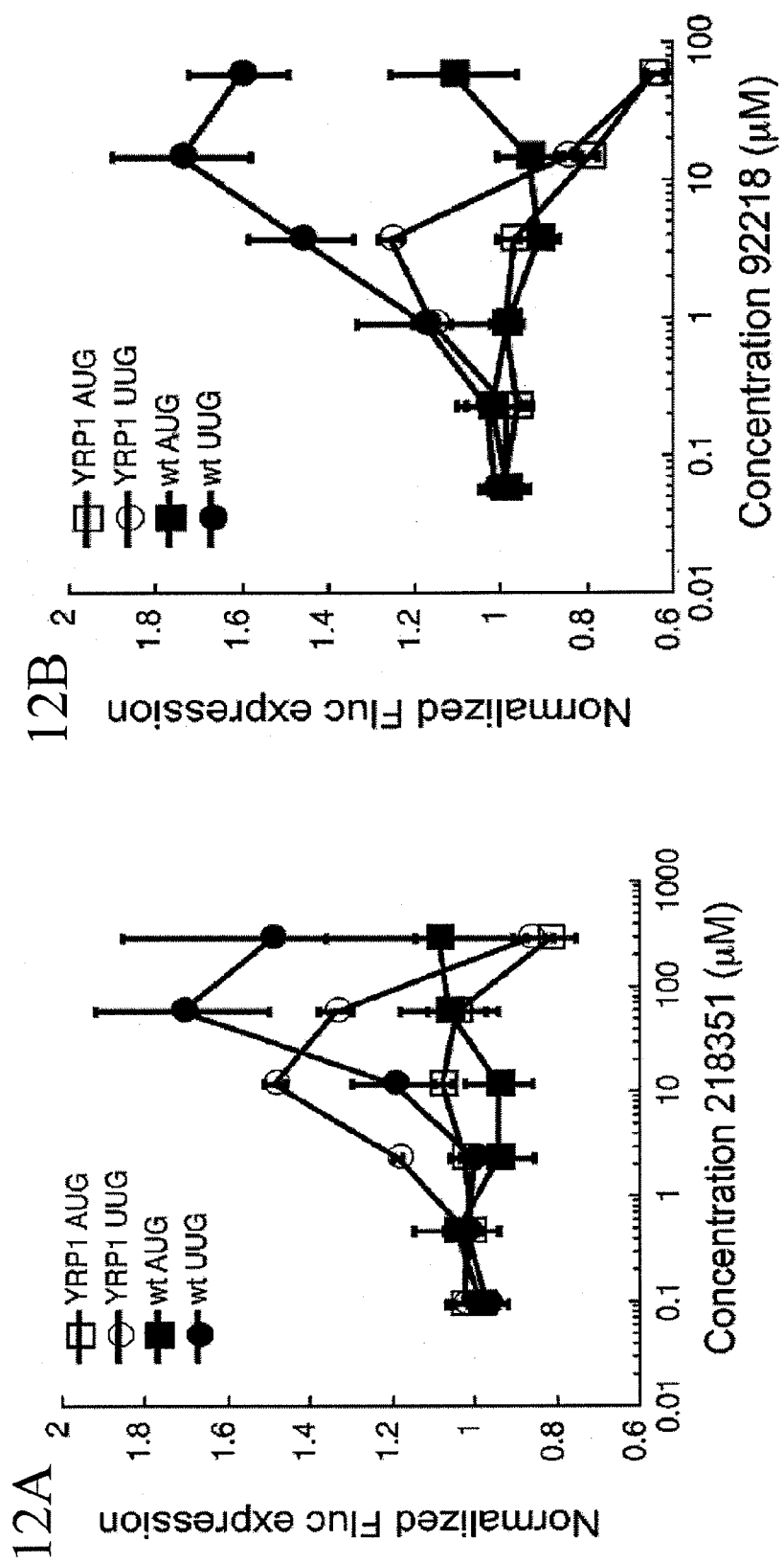
FIG. 12 shows normalized Fluc(AUG) (squares) and Fluc (UUG) (circles) expression in WT yeast (BY4741; closed symbols) and a strain deficient in drug efflux pumps (YRP1: snq2Δ, pdr5Δ, erg6Δ; open symbols) treated with compounds NSC218351 (FIG. 12A) and NSC92218 (FIG. 12B). Points for YRP1 are averages of data from 3 separate transformants ±average deviation.

Another factor possibly contributing to the magnitude of the UUG/AUG ratio change is bioavailability of the molecules. A wild type strain was used in the screen, which may restrict some compounds from entering the cells effectively. Therefore, a strain deficient in efflux pumps (YRP1: snq2Δ, pdr5Δ, erg6Δ) was tested to see if the magnitudes of the effects of the compounds or their effective concentrations would change if efflux from the cells decreased (Kung et al., Proc. Natl. Acad. Sci. U.S.A., vol. 102, no. 10, pp. 3587-3592, 2005). The minimal effective concentration for both compounds is lower in the YRP1 strain than the WT (FIGS. 12A and 12B), suggesting that the compounds act inside of the cell rather than affecting translation by binding to its surface or by altering some other external property. Interestingly, the magnitudes of the UUG/AUG ratio decreased, rather than increased, in the YRP1 strain. A potential explanation for this phenomenon is that the toxic concentrations of the compounds are lowered in the YRP1 strain because of the loss of the efflux pumps, and the leftward shift of the toxicity curve is greater than the shift of the efficacy curve. If this were true it would suggest that the targets of the compounds that produce toxicity are different than those that alter the UUG/AUG initiation ratio. Alternatively, the differences in the effects of the compounds on the UUG/AUG expression ratio could be due to differences in genetic backgrounds of the wild type strain used in the screen (BY4741) and the YRP1 strain.

Structure-Activity Analysis

Two active compounds were identified in different sections of the NCI DTP library, but bear resemblance in structure and activity. Both compounds increase the UUG/AUG ratio by 1.8-fold, but the minimal concentration required to achieve this effect is 4-fold higher for NSC218351 than for NSC92218 (60 µM and 15 µM, respectively). Little information is available about the biological activity of either of these compounds. Studies indicate that compounds related to NSC92218 have anti-fungal activity through an unknown mechanism (Gershon et al., *J. Pharm. Sci.*, vol. 80, no. 6, pp. 542-544, 1991). NSC218351 and derivatives have been implicated in inhibition of protein kinases (Lu et al., *Biol. Chem. Hoppe Seyler*, vol. 377, no. 6, pp. 373-384, 1996).

Figure 13:
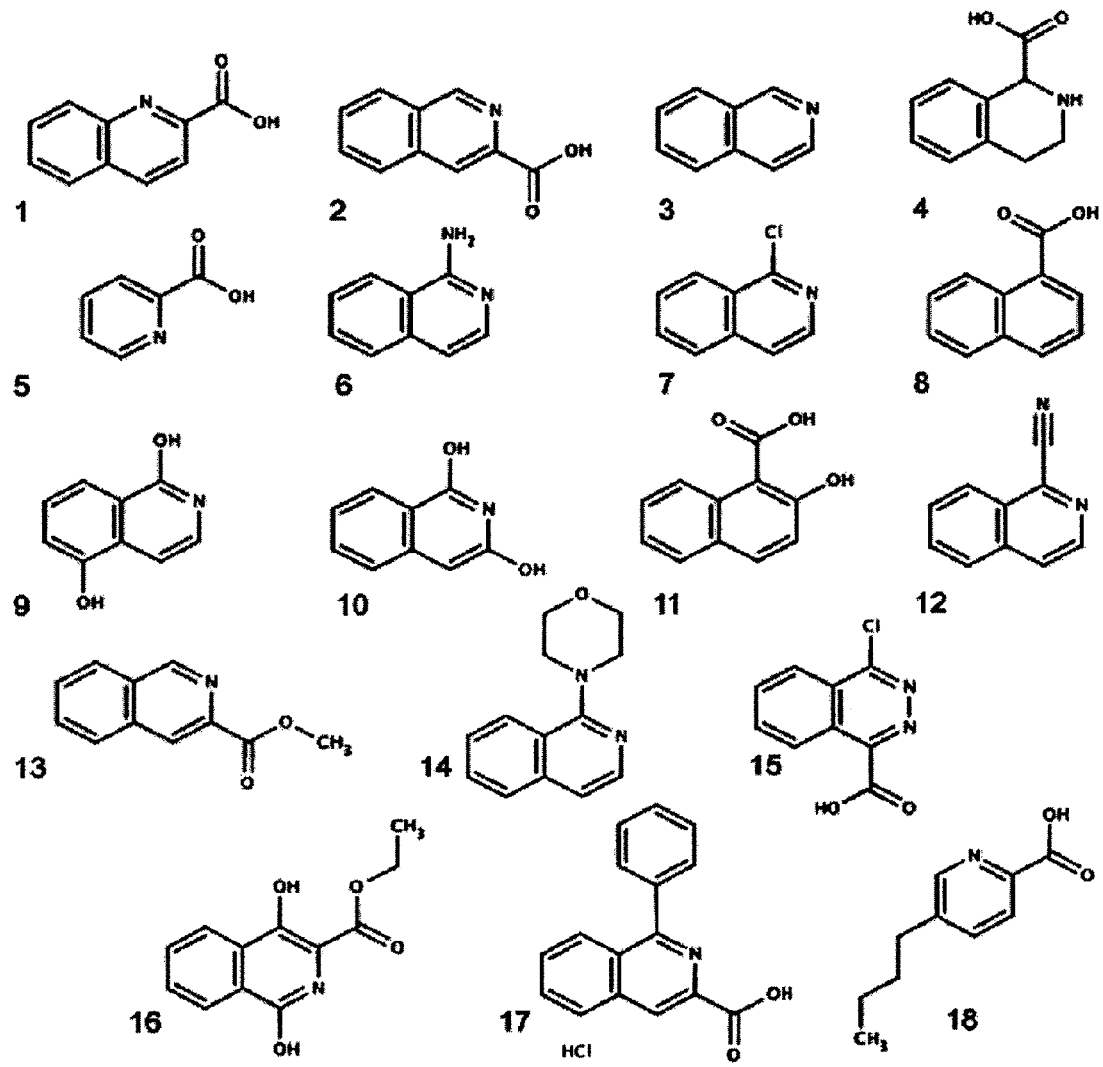
FIG. 13 shows analogs of NSC218351 that were tested at various concentrations in the dual luciferase assay to measure their effects on initiation at UUG and AUG codons.

To learn about the important chemical features of these compounds, about 20 analogs of each were obtained and tested in the dual luciferase assay. Changing some functional groups of NSC218351 (moving or removing the N or acid group, eliminating aromaticity or removing one of the rings) resulted in a loss of the effect on start codon recognition (FIG. 13 and Table 1). Some analogs did change the UUG/AUG expression ratio, but these compounds have similar effects on the AUG/AUG expression ratio indicating that they are not specifically altering the fidelity of translation initiation (compare columns UUG/AUG to AUG/AUG).

TABLE 1

Analogs of NSC218351 tested in the dual luciferase assay. Compound number refers to FIG. 13. Primary screen (UUG/AUG) and counter screen (AUG/AUG) effects are listed, as well as concentration.

| Cpd # | Name (NSC#) | UUG/ AUG | AUG/ AUG | Concentration (µM)* |
|---|---|---|---|---|
| 1 | Quinaldic acid (4882) | 1.00 | 0.71 | 120 |
| 2 | 3-isoquinolinecarboxylic acid (53385) | 1.07 | 1.11 | 60 |
| 3 | Isoquinoline | 0.77 | 0.88 | 120 |
| 4 | 1,2,3,4-tetrahyrdo-1-isoquinoline carboxylic acid | 0.98 | 0.92 | 75 |
| 5 | 2-Picolinic acid | 0.92 | 0.95 | 60 |
| 6 | 1-Aminoisoquinoline | 1.16 | 1.11 | 75 |
| 7 | 1-Chloroisoquinoline | 1.03 | 0.97 | 60 |
| 8 | 1-Naphthoic acid | 1.52 | 1.48 | 60 |
| 9 | 1,5-Isoquinolinediol (65585) | 0.98 | 0.94 | 60 |
| 10 | 1,3-isoquinolinediol (72173) | 0.91 | 1.05 | 60 |
| 11 | 2-Hydroxy-1-naphthoic acid | 0.94 | 1.13 | 60 |
| 12 | 1-isoquinolinecarbonitrile (203335) | 0.78 | 0.71 | 120 |
| 13 | Methyl 3-isoquinolinecarboxylate | 0.94 | 0.78 | 120 |
| 14 | 1-Morpholin-4-yl-isoquinoline (72173) | 0.92 | 0.90 | 60 |
| 15 | 4-chloro-1-phthalazinecarboxylic acid | 0.96 | 0.95 | 60 |

TABLE 1-continued

Analogs of NSC218351 tested in the dual luciferase assay. Compound number refers to FIG. 13. Primary screen (UUG/AUG) and counter screen (AUG/AUG) effects are listed, as well as concentration.

| Cpd # | Name (NSC#) | UUG/ AUG | AUG/ AUG | Concentration (µM)* |
|---|---|---|---|---|
| 16 | Ethyl 1,4-dihydroxyisoquinoline-3-carboxylate (28791) | 1.03 | 0.75 | 75 |
| 17 | 1-phenylisoquinoline-3-carboxylic acid hydrochloride (10181) | 0.94 | 0.89 | 75 |
| 18 | Fusaric acid (19870) | 1.25 | 1.13 | 24 |

*A range of concentrations was tested for each compound, but only one is listed.

Figure 14:
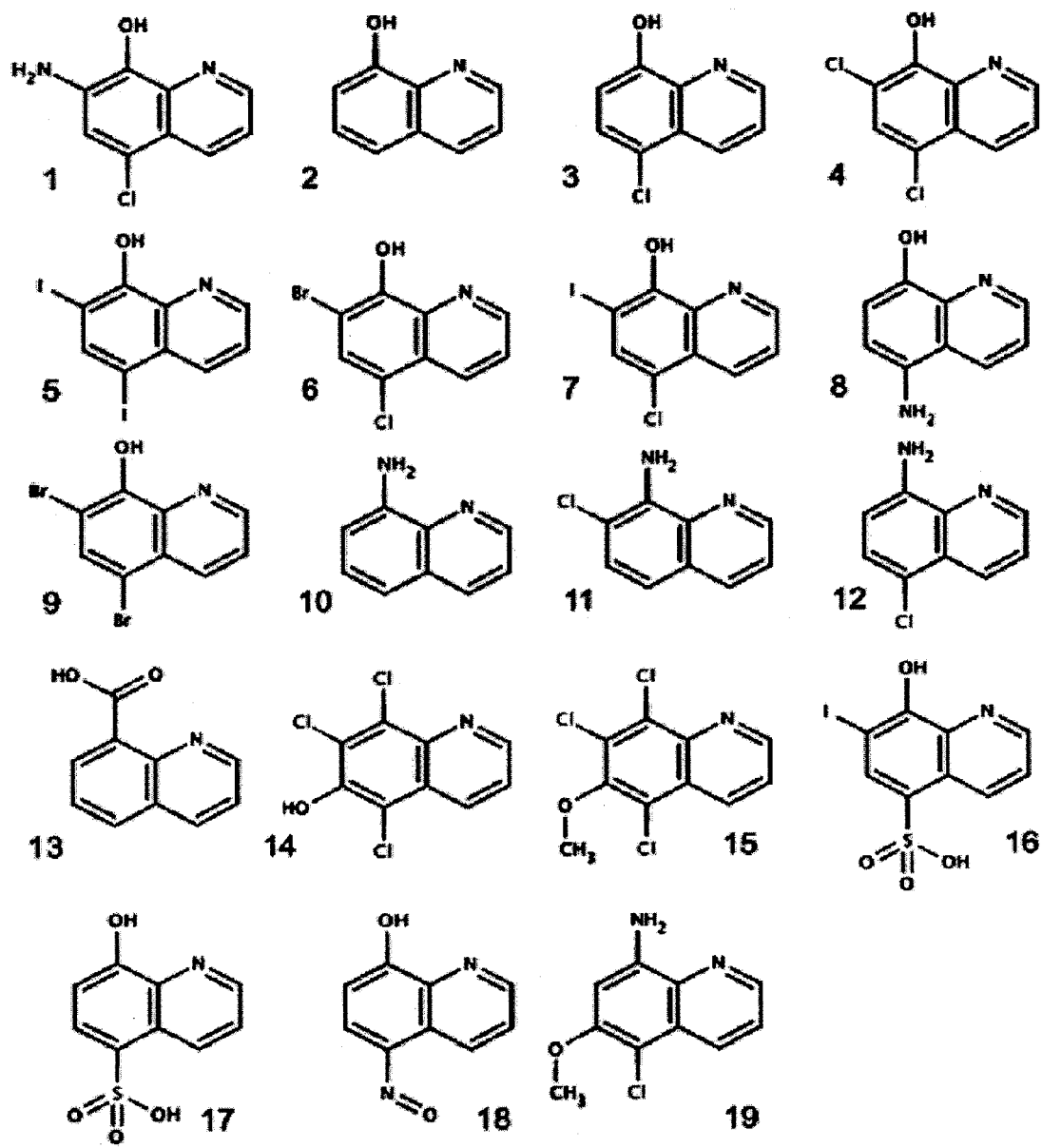
FIG. 14 shows analogs of NSC92218 that were tested at various concentrations in the dual luciferase assay to measure their effects on initiation at UUG and AUG codons.

Fewer close analogs of NSC92218 were available, but changing —I to —Cl, or removing the amine and —I resulted in a loss of the effect (FIG. 14 and Table 2). These data indicate that the activities of NSC92218 and NSC218351 in altering the fidelity of start codon recognition are specific and are not possessed by many structurally similar molecules.

TABLE 2

Analogs of NSC92218 tested in the dual luciferase assay. Compound number refers to FIG. 14. Primary screen (UUG/AUG) and counter screen (AUG/AUG) effects are listed, as well as concentration.

| Cpd # | Name (NSC#) | UUG/ AUG | AUG/ AUG | Concentration (µM)* |
|---|---|---|---|---|
| 1 | 7-amino-5-chloroquinolin-8-ol | 0.94 | 0.81 | 8 |
| 2 | quinolin-8-ol (2039) | 0.81 | 0.99 | 8 |
| 3 | 5-chloroquinolin-8-ol | 1.35 | 1.40 | 60 |
| 4 | 5,7-dichloroquinolin-8-ol (3904) | 1.69 | 1.27 | 8 |
| 5 | 5,7-diiodoquinolin-8-ol (8704) | 1.08 | 1.45 | 8 |
| 6 | 7-bromo-5-chloroquinolin-8-ol | 6.03 | 5.21 | 60 |
| 7 | 5-chloro-7-iodoquinolin-8-ol (3531) | 2.02 | 1.67 | 8 |
| 8 | 5-aminoquinolin-8-ol | 1.09 | 1.14 | 60 |
| 9 | 5,7-dibromoquinolin-8-ol (1810) | 2.10 | 1.72 | 1.6 |
| 10 | quinolin-8-amine (7933) | 0.96 | 0.93 | 8 |
| 11 | 7-chloroquinolin-8-amine (13569) | 1.00 | 1.08 | 8 |
| 12 | 5-chloroquinolin-8-amine (13700) | 1.01 | 1.05 | 8 |
| 13 | quinoline-8-carboxylic acid (6505) | 1.05 | 1.05 | 8 |
| 14 | 5,7,8-trichloroquinolin-6-ol (13207) | 0.89 | 0.88 | 8 |
| 15 | 5,7,8-trichloro-6-methoxyquinoline (13211) | 1.01 | 0.93 | 8 |
| 16 | 8-hydroxy-7-iodoquinoline-5-sulfonic acid (3784) | 0.96 | 1.05 | 8 |
| 17 | 8-hydroxyquinoline-5-sulfonic acid (13139) | 0.94 | 0.96 | 8 |
| 18 | 5-nitrosoquinolin-8-ol (3852) | 1.00 | 0.99 | 8 |
| 19 | 5-chloro-6-methoxyquinolin-8-amine (1184) | 0.94 | 0.99 | 8 |

*A range of concentrations was tested for each compound, but only one is listed.
**JL indicates a gift of Dr. Jun Liu, Johns Hopkins University.

Secondary Assays

Figure 15:
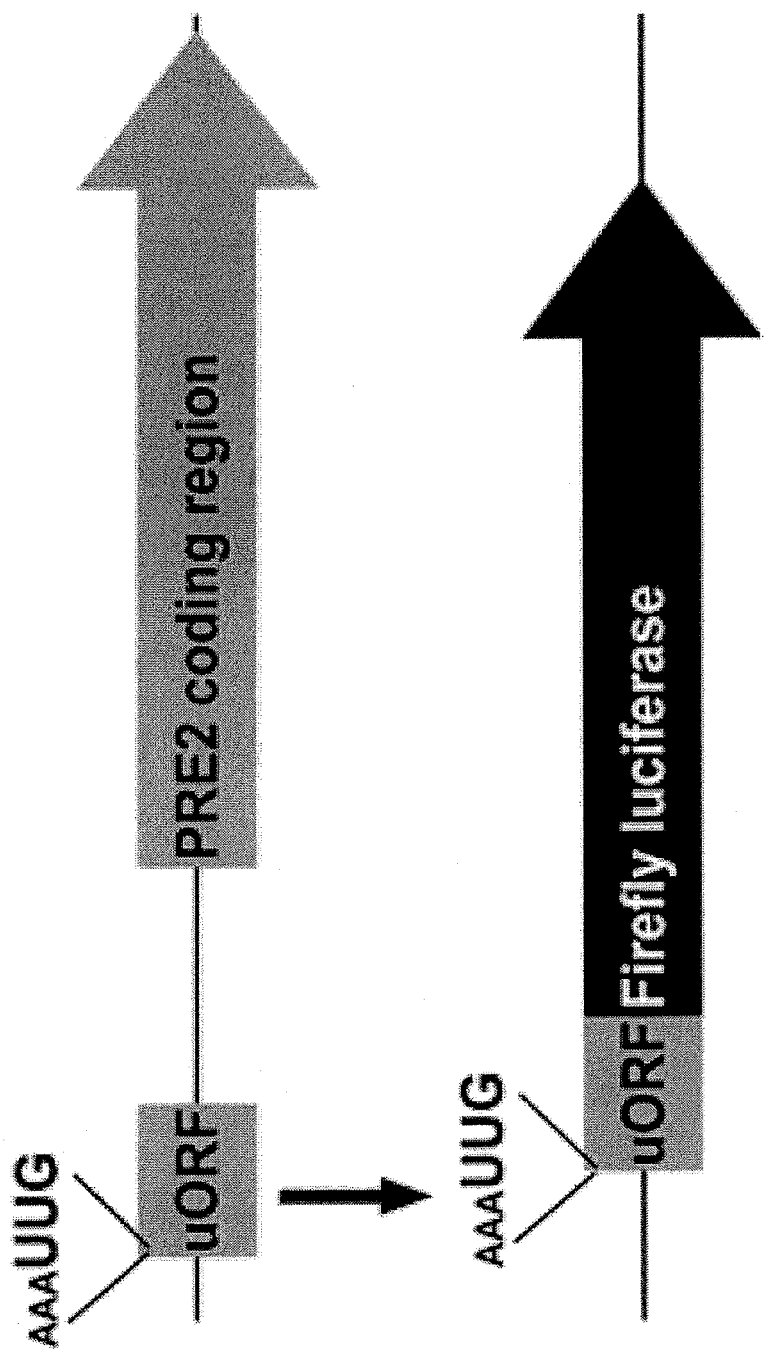
FIG. 15 shows a schematic of the reporter for measuring how compounds increase translation of a luciferase reporter fused to the small, endogenous uORF from PRE2 beginning with a UUG codon. As a control, the uORF was fused out of frame from the luciferase coding region.
Figure 16:
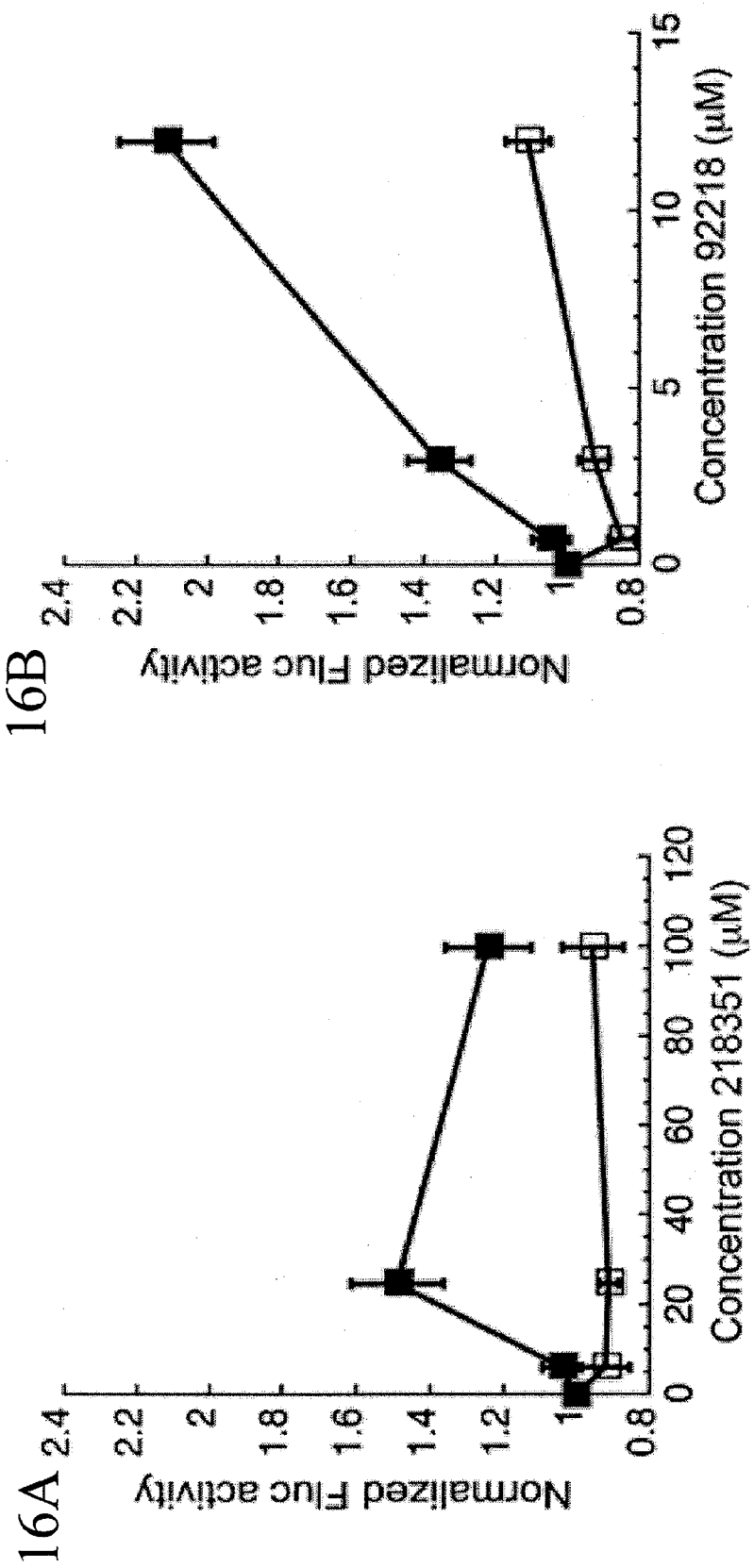
FIG. 16 shows BY4741 expressing the reporter from FIG. 14 treated with NSC218351 (FIG. 16A) or NSC92218 (FIG. 16B), and Fluc activity was measured. Closed squares are the in-frame reporters, and open squares are the out-of-frame controls. Fluc activity with DMSO alone was used to normalize the activity with compound. Points are averages of 2 independent experiments ±average deviation.

Ribosomal profiling identified over 100 small upstream open readings frames (uORFs) that appear to be translated from non-AUG start codons in *S. cerevisiae* (Ingolia et al., *Science*, vol. 324, no. 5924, pp. 218-223, 2009). uORFs are coding regions that are sometimes used to regulate the translation of a downstream ORF encoding a protein (Meijer et al., *Biochem. J.*, vol. 367 (Pt. 1), pp. 1-11, 2002). To demonstrate that the compounds have a general effect on the fidelity of start codon recognition, rather than a specific one on the use of the start codon in Fluc mRNA, an uORF identified by Ingolia and colleagues from PRE2 mRNA was fused to the firefly luciferase coding sequence. This construct was used to assess the effect of the compounds on translation mediated by the non-AUG start codon of the uORFs. The PRE2 uORF has an UUG start codon, with the consensus sequence (−3)AAA (−1) directly upstream of UUG (FIG. 15). In the control reporter, the luciferase coding region is out-of-frame from the start codon of the uORF. In wild type yeast, NSC218351 and NSC92218 increase expression of the reporter approximately 1.5-fold and 2-fold, respectively (FIGS. 16A and 16B), similar to their effects in the dual luciferase assay. The out-of-frame controls are not well translated, and incubation with either compound does not improve luciferase signal. RT-qPCR showed that the compounds do not increase mRNA levels of these reporters (data not shown), indicating that the increase in luciferase signal is due to a decrease in the fidelity of start codon selection.

Yeast Growth Assays Using Sui⁻ Phenotype

Figure 17:
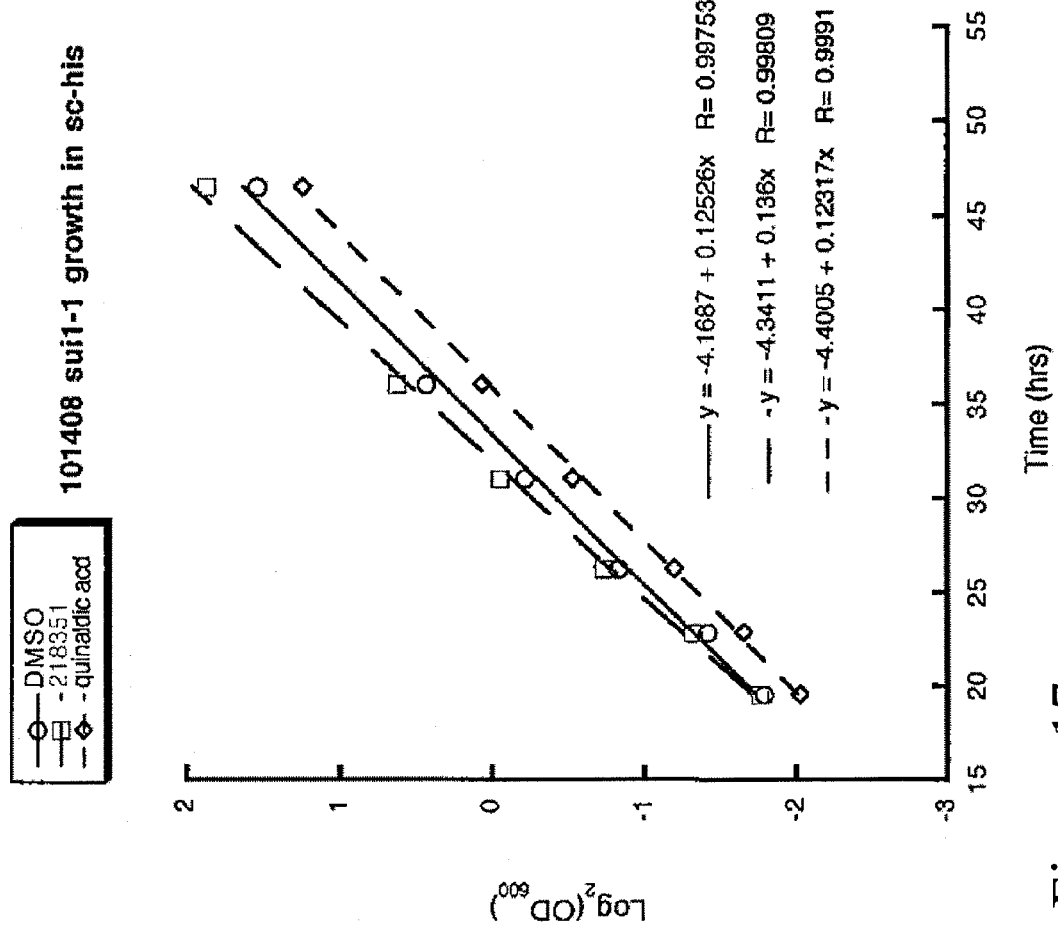
FIG. 17 shows growth of Sui⁻ mutant eIF1 D83G with compound NSC 218351, DMSO, or analog quinaldic acid in SC-His media. Doubling times were quantified for two experiments by plotting $Log_2(OD_{600})$ vs. time. The slope of the line between $-2.5<Log_2(OD_{600})<2$ equals 1/doubling time.

NSC 218351 enhances the growth of the eIF1 Sui⁻ strains on His⁻ plates. In His⁻ culture, the doubling time of eIF1 D83G was decreased from 8 hrs to 7.35 hrs (FIG. 17). While small, the effects are reproducible. No effects on growth of Sui⁻ strains with mutations in other initiation factors (eIF1A, eIF2, and eIF5) have been detected.

Figure 18:
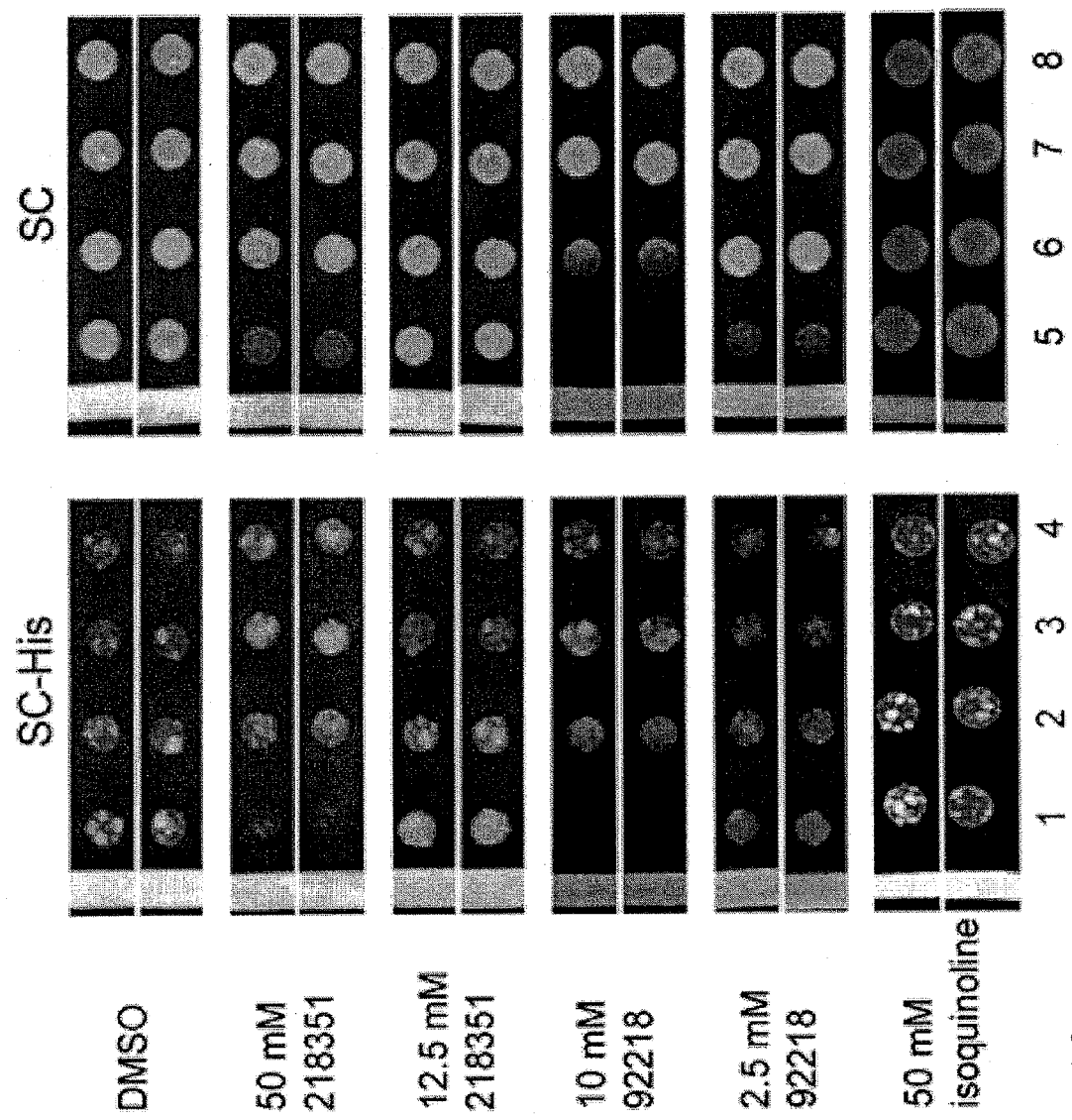
FIG. 18 shows that both compounds increase the growth of Sui⁻ strain sui1-1 (eIF1 D83G) on media lacking histidine. Compound or solvent soaked paper strips were placed on agar plates. Yeast were spotted onto the plate as 4 rows increasingly distant from the paper strip and grown for 4 days on SC-His and 2 days on SC. Two rows from one representative experiment are shown (the 50 mM isoquinoline data are from a separate experiment). The results were consistent in all rows and in three independent experiments.

Chemically increasing use of near-cognate codons as start codons mimics the Sui⁻ phenotype. Sui⁻ mutations were originally identified in a screen that requires translation initiation at a non-AUG start codon in a mutant of the HIS4 gene (his4-303 allele) for growth on SC-His media (Donahue et al., *Mol. Cell. Biol.*, vol. 8, no. 7, pp. 2955-2963, 1988). Compounds that increase the use of non-AUG start codons to a small degree should further increase growth of Sui⁻ strains with the his4-303 allele on SC-His media, chemically enhancing the Sui⁻ phenotype. To test this, a paper strip saturated with compound was placed onto a plate of media (SC or SC-His). Yeast with the his4-303 allele was spotted on the plate at various distances from the compound- or solvent-containing strips. DMSO alone does not affect growth of the Sui⁻ strain (sui1-1) on complete media (SC) or selective media (SC-His) (FIG. 18). Close to the compound source, 10 mM NSC92218 prevented growth and 50 mM NSC218351 slowed growth (FIG. 18, column 1 and 5). In the presence of 50 mM NSC218351 on the paper strip, growth of sui1-1 on selective media was inhibited close to the drug source, but was enhanced relative to the DMSO farther from the source (FIG. 18, compare columns 1, 3 and 4). With 12.5 mM NSC218351, growth of the sui1-1 strain is enhanced in the column closest to the compound source on SC-His (column 1). In columns 2 and 3, 10 mM NSC92218 enhanced growth of the sui1-1 strain on SC-His, especially when normalized for the inhibitory effect on growth on the SC plate (columns 2 vs. 6). With 2.5 mM NCS92218, growth enhancement occurred in column 1 on SC-His relative to the inhibitory effect on SC (columns 1 vs. 5). Thus both compounds enhance the phenotype of a Sui⁻ strain of yeast at discrete distances from the compound source on SC-His media. The analog isoquinoline (FIG. 13, compound 3) did not cause any enhancement of growth in this assay, further indicating specificity of the effects produced by NSC218351 and NSC92218.

Role of Start Codon Context

In addition to identifying compounds that alter the fidelity of start codon recognition, this screen has the potential to identify compounds that affect recognition of the consensus sequence elements flanking start codons in yeast. The yeast consensus sequence is AAAA directly upstream of the initiation codon (Hamilton et al., Nucleic Acids Res., vol. 15, no. 8, pp. 3581-2593, 1987; Shabalina et al., Nucleic Acids Res., vol. 32, no. 5, pp. 1774-1782, 2004). In mammals, the consensus sequence is GCC(A/G)CC$_{AUG}$G (SEQ ID NO: 8), and can have up to a 20-fold effect on use of the codon as a start site (Kozak M., *Cell*, vol. 44, no. 2, pp. 283-292, 1986; Kozak M., *Nucleic Acids Res.*, vol. 15, no. 20, pp. 8125-8148, 1987). In yeast the consensus sequence generally has a small or no effect on initiation from AUG start codons (Cigan et al., *Mol. Cell. Biol.*, vol. 8, no. 7, pp. 2964-2975, 1988; Donahue et al., *Mol. Cell. Biol.*, vol. 8, no. 7, pp. 2955-2963, 1988), but it does have a strong effect on use of non-AUG start codons (Zitomer et al., *Mol. Cell. Biol.*, vol. 4, no. 7, pp. 1191-1197, 1984; Chen et al., *J. Biol. Chem.* vol. 283, no. 6, pp. 3173-3180, 2008). If the firefly reporter with a UUG start codon lacks the consensus sequence (GCTC instead of AAAA), the mRNA is not detectably translated. Since non-AUG codons are more sensitive to this sequence than are AUG codons, the screen might identify compounds that diminish or enhance the influence of the flanking region. Such an effect has not previously been noted in yeast, by genetic mutation or chemical treatment.

In the reporters used for the screen, both the AUG and UUG start codons had AAAA directly upstream (positions −4 to −1). Although the sequence GCTC does not detectably promote translation from a UUG start codon, changing the −3 position to an A in this context (GATC) restores 18% of the signal observed with AAAA (data not shown). Changing any other single upstream position to A does not allow detectable translation from UUG. The Fluc reporter with this minimal stimulatory flanking sequence, GATC, was used to test whether the compounds increase the influence of the sequence upstream of the start codon. The effects of the compounds on Fluc-UUG expression was unchanged when the full (AAAA) upstream sequence was replaced with the minimal version (GATC; data not shown), indicating that the compounds' abilities to increase use of UUG as an initiation codon are not altered by changing the strength of the sequence context around the start codon, and that upstream bases at the −1, −2 and −4 positions are not required for the activity of the compounds.

In Vitro Transcription Assays

An in vitro translation system was also used. This assay uses yeast extracts to translate in vitro transcribed mRNAs encoding *Renilla* luciferase with an AUG or UUG start codon.

No significant effects have been observed in the in vitro translation system; this assay, however, is not very sensitive. When a strong Sui⁻ protein, e.g., eIF5 G31R, was added to wild type extracts, no effect on the fidelity of translation initiation in the in vitro system was observed. eIF1 G107R mutant, which increases translation from UUG in vivo approximately five-fold from wt, increases translation greater than two-fold when added to wild type lysates in the in vitro translation assay. Based on the effect of these Sui⁻ mutants, it seems unlikely that the in vivo effect of NSC 218351 (<two-fold) would be detectable in the in vitro translation system.

Toxicity to Yeast and Mammalian Cells

NSC218351 was not toxic to yeast cells. Growth was reduced at 300 μM, but at working concentrations (10-100 μM) toxicity is not a concern. Mammalian cells have not been tested.

Mechanism of Action

Figure 19:
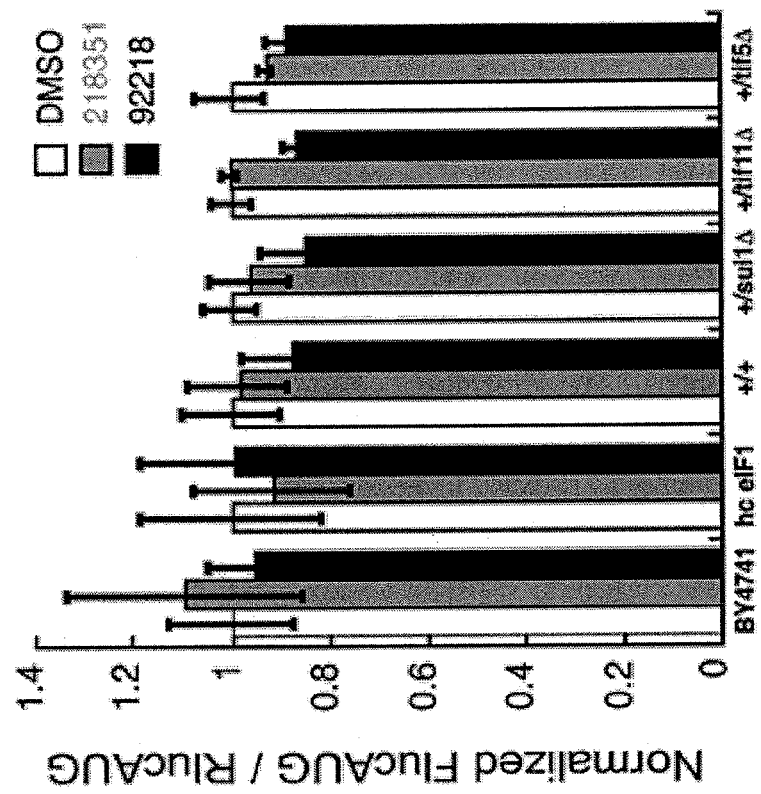
FIG. 19 shows the effect of NSC218351 and NSC92218 on start site selection in strains of yeast with altered levels of eIFs 1, 1A and 5.
Figure 19:
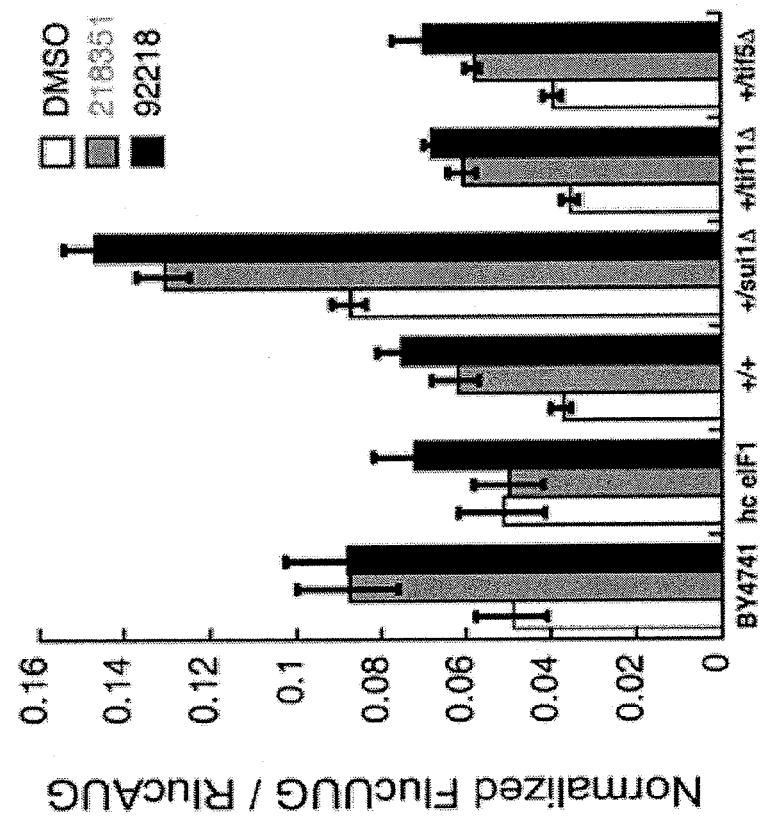
Figure 20:
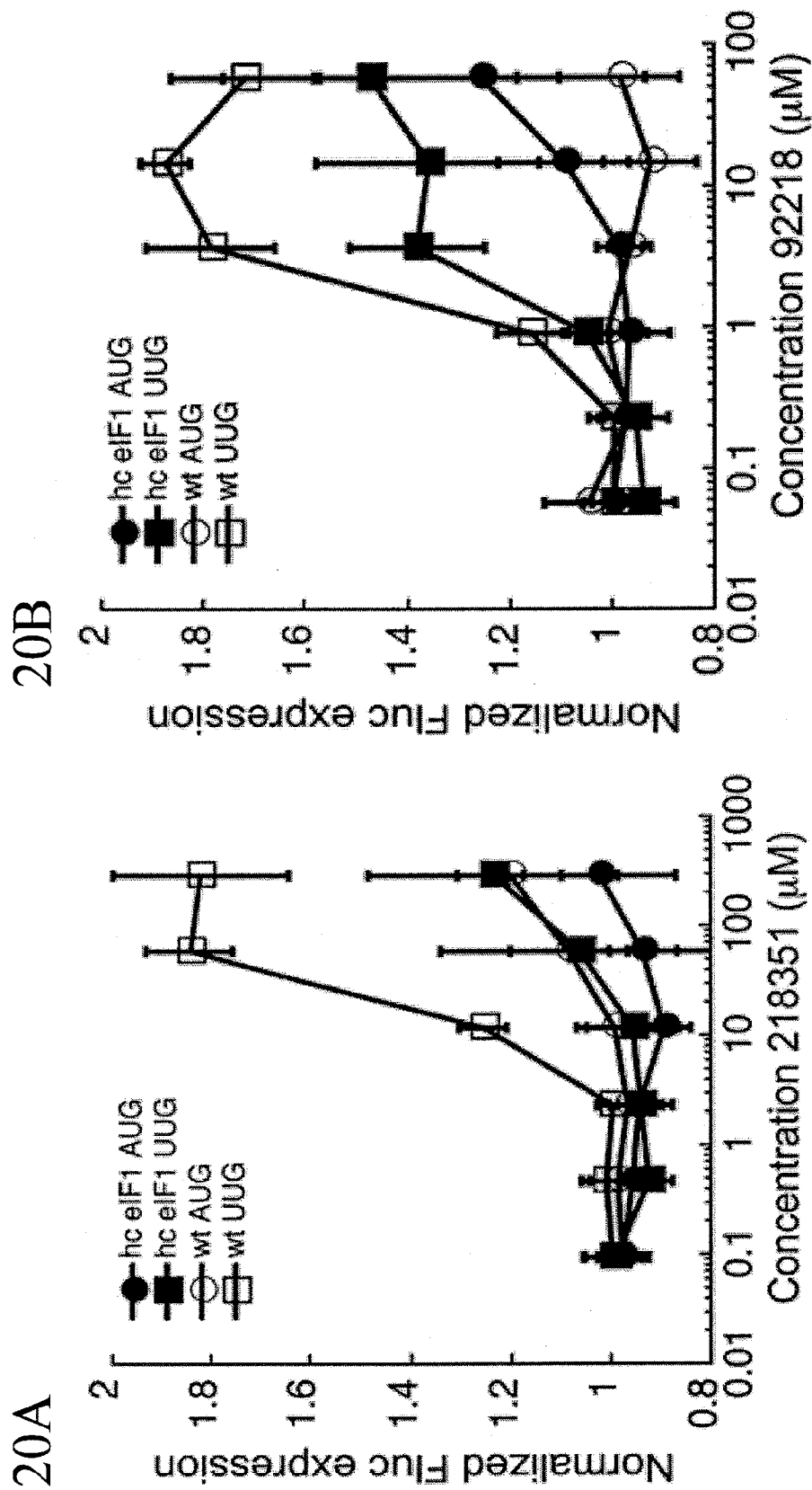
FIG. 20 shows the concentration dependence of the effect of NSC218351 (FIG. 20A) and NSC92218 (FIG. 20B) on Fluc expression from UUG (squares) and AUG (circles) in hc eIF1 (closed symbols) and wild type (open symbols). Data, from 2 independent experiments, were analyzed.

Genetic approaches enabled testing for synthetic effects, either enhancement or suppression, of the compounds with particular yeast genes. eIF1, eIF1A and eIF5 play crucial roles in start codon selection (Mitchell et al., *J. Biol. Chem.*, vol. 283, no. 41, pp. 27345-27349, 2008). To examine the importance of these factors on the effects of the compounds, translation from the UUG start codon of Fluc using the dual luciferase assay in diploid strains haplo-insufficient was measured for these factors (Open Biosystems) (deletion of any one of these factors in haploids is lethal) (Winzeler et al., *Science*, vol. 285, no. 5429, pp. 901-906, 1999). Western analysis demonstrated that the level of each protein in the halpo-insufficient dipoids strains decreased ~2-fold relative to the level in the diploid wild type strain, as expected (data not shown). Haplo-insufficiency of eIF1A (+/tif11Δ) or eIF5 (+/tif5Δ) did not have an effect on translation from UUG (FlucUUG/RlucAUG), but eIF1 haplo-insufficiency (+/sui1Δ) increased use of UUG ~2 fold (FIG. 19A, white bars), consistent with its role as a master switch that controls the response to start codon recognition (Lorsch et al., *J. Biol. Chem.*, vol. 285, no. 21203-21207, 2010). In all of these strains, the compounds still increased the UUG/AUG ratio ~2 fold (FIG. 19A, gray and black bars). This indicates that the effects of eIF1 haplo-insuffciency and the presence of either compound on start codon selection are additive, and that a haplo-insufficiency of eIF1A or eIF5 does not alter the effect of the compounds. The FlucAUG/RlucAUG ratio was not altered in any of these strains or conditions (FIG. 19B), indicating that the effects of the compounds in these strains are specific to translation from a near cognate start codon and that haploinsufficiency of eIF1 reduces the fidelity of start codon recognition rather than generally affecting Fluc expression or activity.

codon recognition. The effect of NSC218351 was completely suppressed in a strain over-expressing eIF1 (FIG. 19A, compare gray bars of BY4741 and hc eIF1; FIG. 20A, compare open and closed squares), and the effect of NSC92218 was reduced by ~50% relative to the effect in wild type cells (FIG. 19A, compare black bars of BY4741 and hc eIF1; FIG. 20B, compare open and closed squares). Because over-expression of eIF1 alone does not increase the fidelity of start codon selection, this suppression is specific to the Sui⁻ phenotype, whether mutationally or chemically induced, and provides evidence that the compounds affect the fidelity of translation initiation by altering the function of the 40S ribosomal subunit or one of the initiation factors that participate in start codon selection.

Example 3

Additional Compounds

Additional compounds identified by the described screening method are shown below.

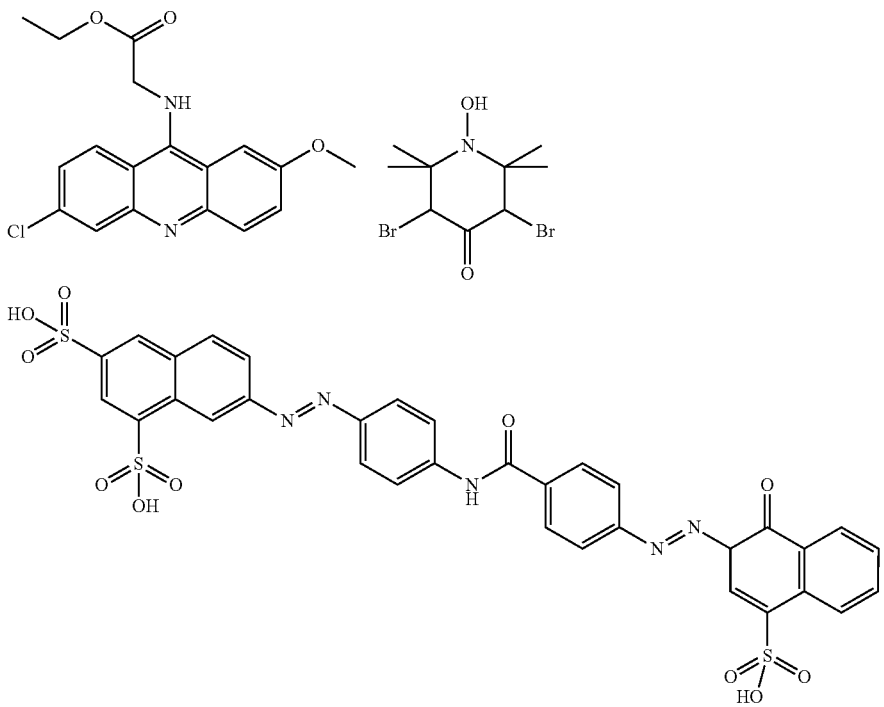

Although a deficiency in eIF1 decreases the fidelity of translation initiation, over-expression of eIF1 does not increase the fidelity of start site selection in WT yeast (Cheung et al., *Genes Dev.*, vol. 21, no. 10, 1217-1230, 2007) (FIG. 19A, compare white bars of BY4741 and hc eIF1). However, over-expression of eIF1 has been shown to suppress the Sui⁻ phenotypes of a number of mutations in eIF1 and other factors (eIF1A, eIF5, eIF3, eIF213 and eIF4G) (Cheung et al., *Genes Dev.*, vol. 21, no. 10, 1217-1230, 2007; Saini et al., *Genes Dev.*, vol. 24, no. 1, pp. 97-110; 2010; Valasek et al., *Mol. Cell. Biol.*, vol. 24, no. 21, pp. 9437-9455, 2004; He et al., *Mol. Cell. Biol.*, vol. 23, no. 15, pp. 5431-5445, 2003). Interestingly, over-expression of eIF1 also suppressed the effects of both compounds on the fidelity of start According to the invention a dual luciferase assay has been adapted into a high-throughput screen to identify compounds that alter the fidelity of start codon recognition in yeast. These structurally related compounds passing the primary screen and the counterscreen increase translation from near-cognate start codons ~2-fold in the dual luciferase assay (at 60 μM NSC218351 and 15 μM NSC92218) and in the uORF-Fluc assay, and enhance the Sui⁻ phenotypes conferred by the sui1-1 D83G eIF1 mutation and by haploinsufficiency of WT eIF1. Thus the compounds decrease the fidelity of start codon selection in three separate in vivo assays. Additionally, the increased use of UUG as a site of initiation caused by NSC218351 and NSC92218 is suppressed, completely and partially, respectively, by over-expression of eIF1, providing strong evidence that the compounds act in a mechanistically similar manner to Sui⁻ mutations in initiation factors.

eIF1 is a key controller of start codon selection (Mitchell and Lorsch 2008). It binds tightly to the 43S PIC and is important for maintaining a scanning competent conformation of the ribosome. Upon start codon recognition, eIF1 is released from the PIC, causing a reversion to the closed, scanning arrested state of the ribosome and triggering release of P, from eIF2 (Lorsch and Dever 2010). Most Sui⁻ mutations in eIF1 act by decreasing the factor's affinity for the PIC and thus increasing the rate of eIF1 release at non-AUG codons. Over-expression of these eIF1 mutants can partially suppress the Sui⁻ phenotype (Cheung et al. 2007). Suppression of the effects of NSC218351 and NSC92218 by hc eIF1 is consistent with the idea that they act by altering eIF1 affinity for the PIC. However, effects of either compound on the affinity of eIF1 for the 40S subunit (+/− eIF1A) or on the rate of release of the factor upon start codon recognition by the PIC (data not shown) were not detected. These data suggest that the compounds act on another step in the pathway and that eIF1 over-expression can suppress the effect on this step. This is consistent with the fact that hc eIF1 can also suppress the Sui⁻ phenotypes of mutations in eIF1A, eIF5, eIF3, eIF4G, and eIF2 (Cheung et al., *Genes Dev.*, vol. 21, no. 10, pp. 1217-1230, 2007; Saini et al., *Genes Dev.*, vol. 24, no. 1, pp. 97-110, 2010; Valasek et al., *Mol. Cell. Biol.*, vol. 24, no. 21, pp. 9437-9455, 2004; He et al., *Mol. Cell. Biol.*, vol. 23, no. 15, pp. 5431-5445, 2003).

In addition to providing new insight into the complicated mechanism of start codon selection, the compounds identified in this screen could serve as leads for the development of new drugs targeting translation initiation. For example, modulators of the fidelity of start codon recognition could be used to treat variants of genetic diseases that are caused by mutations of the start codon or region surrounding the start codon. A compound that functions analogously in translation termination has shown promise for clinical use. The compound, PTC124, specifically increases read-through of non-sense codons in vivo, and is currently in clinical trials to treat cystic fibrosis, Duchenne myscular dystrophy and hemophilia (Welch et al., *Nature*, vol. 447, no. 7140, pp. 87-91, 2007). In addition to treating genetic diseases, compounds that reduce the fidelity of start codon recognition might be developed into anticancer agents, as rapidly reproducing cells could be less tolerant of mis-translation than are quiescent cells. Alternatively, if the effects of the compounds identified here are specific to yeast, they might be developed into novel anti-fungal agents.

This is the first screen to find compounds that alter the fidelity of start codon selection in eukaryotes. The compounds identified bear striking resemblance to each other, yet the ability to decrease the fidelity of start codon selection appears to be quite specific.

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

The invention claimed is:

1. A method of altering the fidelity of eukaryotic translation initiation codon selection, the method comprising administering to a cell a compound of Formula I-V:

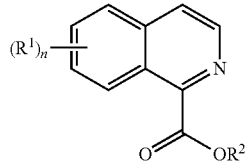
(I)

where n is an integer from 1 to 4; $R^1$ is H, halogen, alkyl, $NO_2$, $OR^3$, $N(R^4)_2$, or $SR^5$; $R^2$ is H or alkyl; $R^3$ is H or alkyl, and $R^4$ is H or alkyl and $R^5$ is H or alkyl;

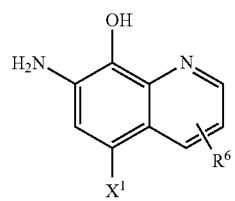
(II)

where $X^1$ is Br or I; $R^6$ is H, halogen, alkyl, $NO_2$, $OR^3$, $N(R^4)_2$, or $SR^5$; $R^3$ is H or alkyl, and $R^4$ is H or alkyl and $R^5$ is H or alkyl;

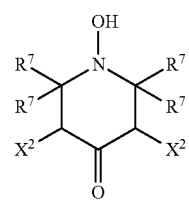
(III)

where $X^2$ is F, Cl, Br, or I; $R^7$ is H or alkyl;

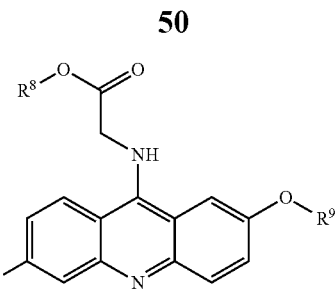
(IV)

where $X^3$ is F, Cl, Br, or I; $R^8$ is H or alkyl; $R^9$ is H or alkyl;

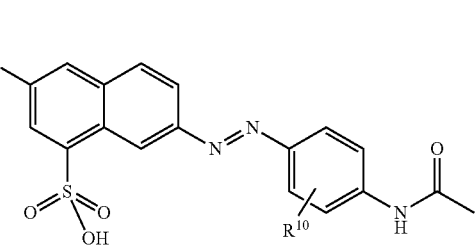
(V)

where $R^{10}$ is H or alkyl and $R^H$ is H or alkyl;

and pharmaceutically acceptable salts thereof.

2. The method of claim 1, wherein the compound is selected from the group consisting of:

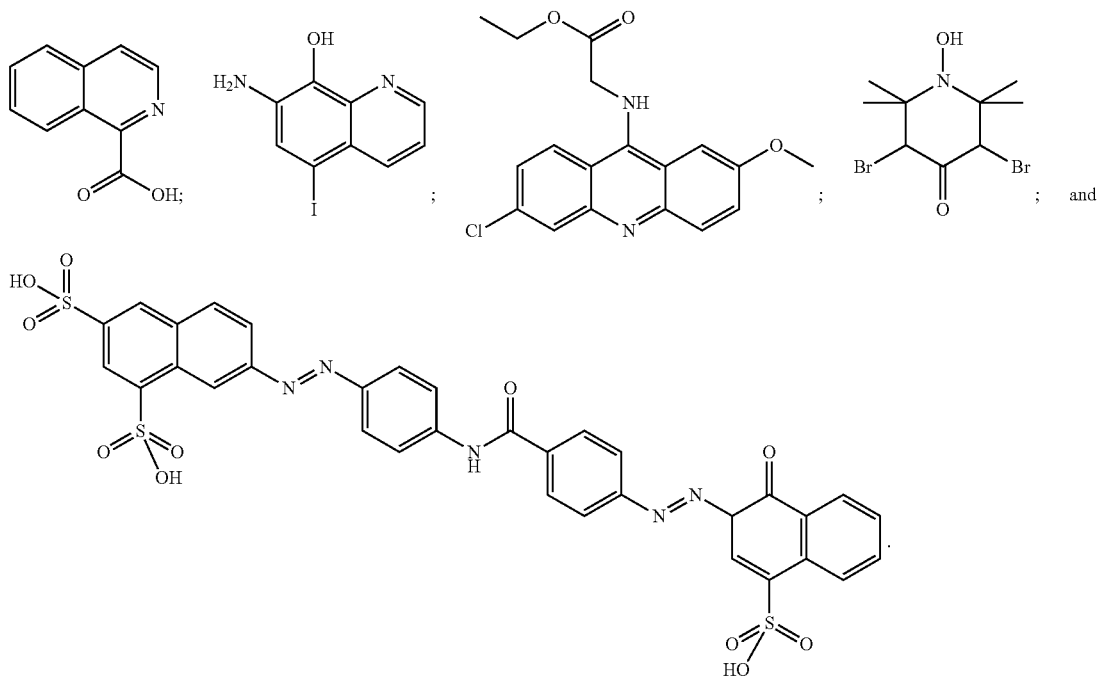

3. The method of claim 1, wherein the compound is

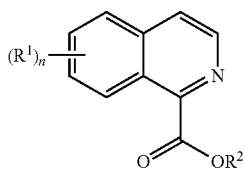
(I)

where n is an integer from 1 to 4; $R^1$ is H, halogen, alkyl, $NO_2$, $OR^3$, $N(R^4)_2$, or $SR^5$; $R^2$ is H or alkyl; $R^3$ is H or alkyl, and $R^4$ is H or alkyl and $R^5$ is H or alkyl; or

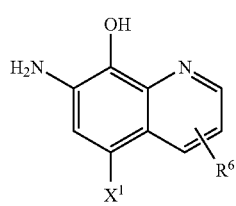
(II)

where $X^1$ is Br or I; $R^6$ is H, halogen, alkyl, $NO_2$, $OR^3$, $N(R^4)_2$, or $SR^5$; $R^3$ is H or alkyl, and $R^4$ is H or alkyl and $R^5$ is H or alkyl.

4. The method of claim 3, wherein the compound is selected from

 and 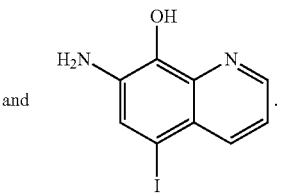.

5. A method of screening a test compound for identifying activity of the test compound in altering the fidelity of translation initiation codon selection, comprising introducing a test compound according to Formula I-V to eukaryotic cells in a culture wherein:

Formula I-V are defined as:

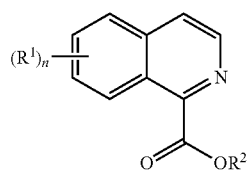
(I)

where n is an integer from 1 to 4; $R^1$ is H, halogen, alkyl, $NO_2$, $OR^3$, $N(R^4)_2$, or $SR^5$; $R^2$ is H or alkyl; $R^3$ is H or alkyl, and $R^4$ is H or alkyl and $R^5$ is H or alkyl;

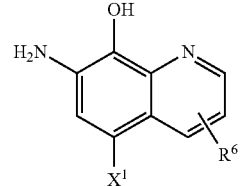
(II)

where $X^1$ is Br or I; $R^6$ is H, halogen, alkyl, $NO_2$, $OR^3$, $N(R^4)_2$, or $SR^5$; $R^3$ is H or alkyl, and $R^4$ is H or alkyl and $R^5$ is H or alkyl;

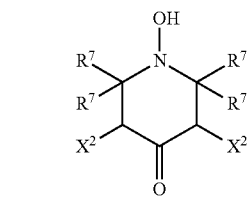
(III)

where $X^2$ is F, Cl, Br, or I; $R^7$ is H or alkyl;

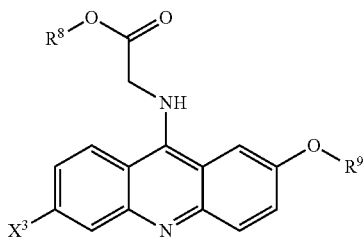
(IV)

where $X^3$ is F, Cl, Br, or I; $R^8$ is H or alkyl; $R^9$ is H or alkyl;

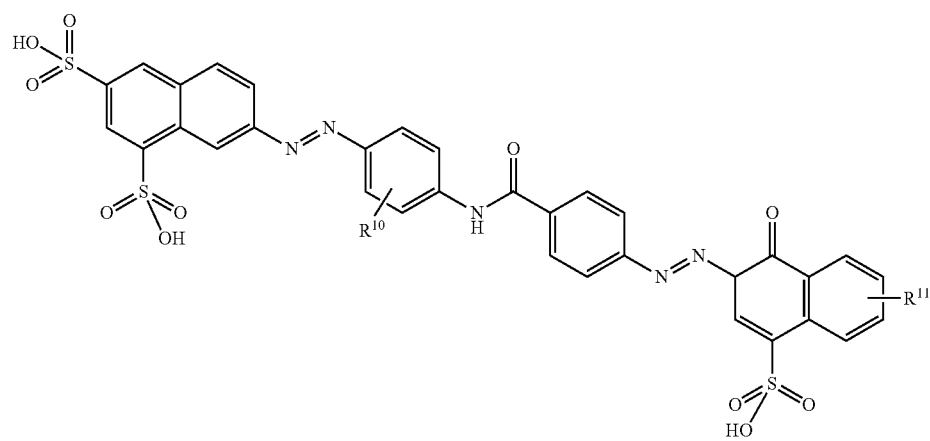
(V)

where $R^{10}$ is H or alkyl and $R^{11}$ is H or alkyl; and pharmaceutically acceptable salts thereof; and the cells comprise a DNA sequence encoding a first reporter protein, where the mRNA from the first reporter protein has an initiation codon that is a near-cognate of AUG, and measuring the change in the amount of reporter protein to identify the activity of the test compound in altering the fidelity of translation initiation codon selection.

6. The method of claim 5 wherein the cell further comprises DNA sequence encoding a second reporter protein, where the mRNA from the second reporter protein has an AUG initiation codon.

7. The method of claim 6, wherein said measuring step comprises measuring the ratio between the amount of first reporter protein and the second reporter protein.

8. The method of claim 5, where the cells are yeast cells.

9. The method of claim 5, where the cells are mammalian cells.

10. The method of claim 5, where the first reporter protein is a luciferase protein.

11. The method of claim 5, where the first reporter protein is a firefly luciferase protein.

12. The method of claim 6, where the second reporter protein is a luciferase protein.

13. The method of claim 6, where the first reporter protein is a firefly luciferase protein and the second reporter is a *Renilla* luciferase protein.

14. A method of treating a disorder comprising administering to a subject in need of treatment an effective amount of a compound selected from the group consisting of

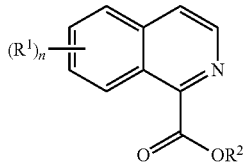

(I)

where n is an integer from 1 to 4; $R^1$ is H, halogen, alkyl, $NO_2$, $OR^3$, $N(R^4)_2$, or $SR^5$; $R^2$ is H or alkyl; $R^3$ is H or alkyl, and $R^4$ is H or alkyl and $R^5$ is H or alkyl;-

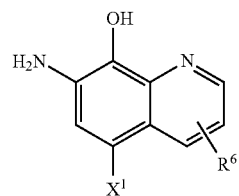

(II)

where $X^1$ is Br or I; $R^6$ is H, halogen, alkyl, $NO_2$, $OR^3$, $N(R^4)_2$, or $SR^5$; $R^3$ is H or alkyl, and $R^4$ is H or alkyl and $R^5$ is H or alkyl;

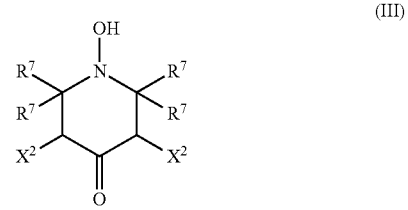

(III)

where $X^2$ is F, Cl, Br, or I; $R^7$ is H or alkyl;

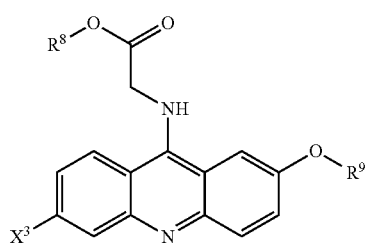

(IV)

where $X^3$ is F, Cl, Br, or I; $R^8$ is H or alkyl; $R^9$ is H or alkyl; and

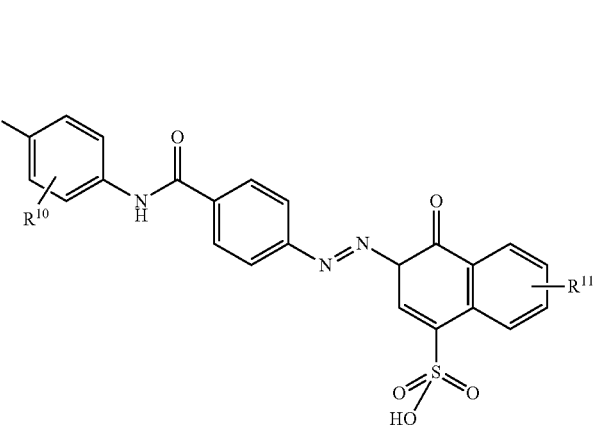

(V)

or pharmaceutically acceptable salt thereof, wherein the disorder is: a disorder characterized by a non-AUG initiation codon.

15. The method of claim 14, wherein the compound is selected from the group consisting of:

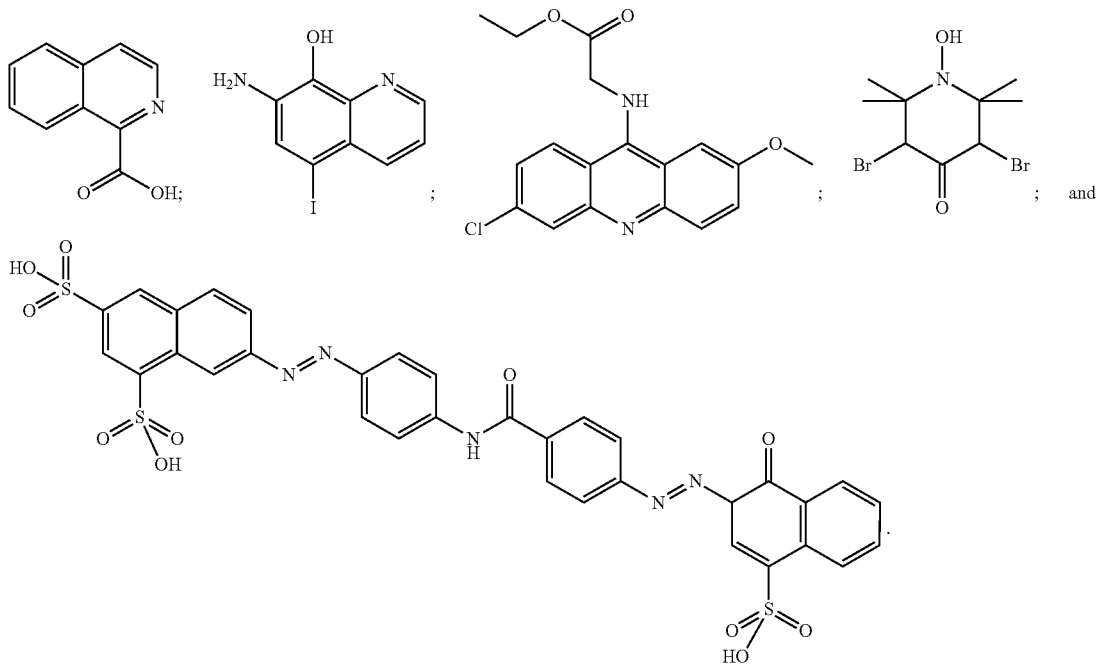

16. The method of claim 14 wherein the compound is

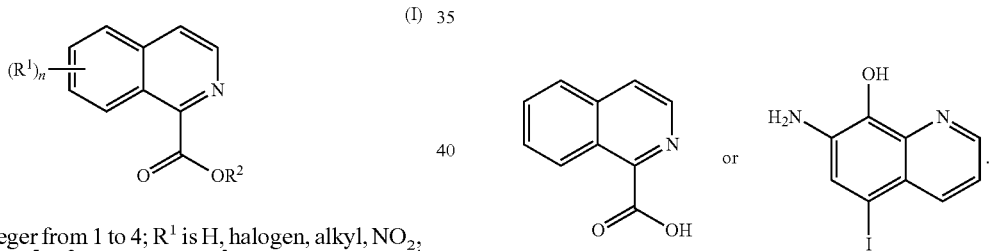

where n is an integer from 1 to 4; $R^1$ is H, halogen, alkyl, $NO_2$, $OR^3$, $N(R^4)_2$, or $SR^5$; $R^2$ is H or alkyl; $R^3$ is H or alkyl, and $R^4$ is H or alkyl and $R^5$ is H or alkyl; or

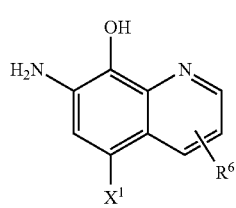

where $X^1$ is Br or I; $R^6$ is H, halogen, alkyl, $NO_2$, $OR^3$, $N(R^4)_2$, or $SR^5$; $R^3$ is H or alkyl, and $R^4$ is H or alkyl and $R^5$ is H or alkyl.

17. The method of claim 16, wherein the compound is

18. The method of claim 14, wherein the disorder is a genetic disorder characterized by a single nucleotide mutation in the initiation codon selected from the group consisting of beta-thalassemia, alpha-thalassemia, hemoglobin H disease, phenylketonuria congenital adrenal hyperplasia Syndrome, and Refsum disease.

19. The method of claim 14, wherein the disorder is a fungal infection.

* * * * *

SEQUENCE LISTING

<160> NUMBER OF SEQ ID NOS: 8

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcaactagtg gaagacgcca aaaacataaa g                                    31

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gctttaatta attacacggc gatctttccg                                      30

<210> SEQ ID NO 3
<211> LENGTH: 38
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 3
gcattaatta atagaattttt gaatttggtt aagaaaag                              38

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gctgggccca tcagagctgg taaattcaag                                        30

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcaactagtt ctattcaatt taatagtaaa tttgttatt                              39

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcaactagta tctattcaat ttaatagtaa atttgttat                              39

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gctgcggccg cgttactatc aagatgtatc aaacaatg                               38

<210> SEQ ID NO 8
<211> LENGTH: 10
<212> TYPE: RNA
<213> ORGANISM: Artificial Sequence
<220> FEATURE:
<223> OTHER INFORMATION: Description of Artificial Sequence: Synthetic
      consensus sequence

<400> SEQUENCE: 8 gccrccaugg                                                              10
```